(12) United States Patent
Taguchi et al.

(10) Patent No.: US 6,415,012 B1
(45) Date of Patent: Jul. 2, 2002

(54) MULTI-SLICE X-RAY COMPUTED TOMOGRAPHY APPARATUS

(75) Inventors: Katsuyuki Taguchi, Tokyo; Tatsuro Suzuki, Tochigi-ken, both of (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/504,962

(22) Filed: Feb. 16, 2000

(30) Foreign Application Priority Data

Feb. 17, 1999 (JP) .......................................... 11-039149

(51) Int. Cl.⁷ ................................................ A61B 6/03
(52) U.S. Cl. ............................................ 378/15; 378/17
(58) Field of Search .............................. 378/4, 15, 17, 378/901

(56) References Cited

U.S. PATENT DOCUMENTS

| 5,974,108 A | 10/1999 | Taguchi et al. | 378/4 |
| 5,999,587 A | * 12/1999 | Ning et al. | 378/4 |
| 6,075,836 A | * 6/2000 | Ning | 378/98.12 |
| 6,118,841 A | * 9/2000 | Lai | 378/19 |

FOREIGN PATENT DOCUMENTS

| JP | 4-224736 | 8/1992 |
| JP | 9-234195 | 9/1997 |
| JP | 10-192269 | 7/1998 |
| JP | 10-243941 | 9/1998 |

* cited by examiner

*Primary Examiner*—David V. Bruce
(74) *Attorney, Agent, or Firm*—Oblon, Spivak, McClelland, Maier & Neustadt, P.C.

(57) ABSTRACT

An X-ray CT apparatus includes an X-ray source for generating X-rays, a detector having detector elements laid out in a plurality of rows in a body axial direction of an object on a couch for detecting X-rays transmitted through the object, and a helical data collector that collects helical data while at least one of a gantry and the couch is moved by a moving device along a body axial direction of the object on the couch in a state that at least one of the gantry and the couch is tilted. A data processor is further provided that reconstructs an image by interpolating the helical data collected and converting it into parallel beam data that is tilt corrected.

16 Claims, 20 Drawing Sheets

Z-AXIAL DIRECTION
SLICE DIRECTION

CROSS-SECTION B

CROSS-SECTION A

Z-AXIAL DIRECTION
SLICE DIRECTION

ZFC1

ZFC2

ZFC3

ZFC4

PARALLEL BEAMS OF pview-th PROJECTION ANGLE

MULTI-SLICE X-RAY COMPUTED TOMOGRAPHY APPARATUS

BACKGROUND OF THE INVENTION

1. Field of the Invention

The present invention relates to an X-ray CT (Computed Tomography) apparatus. More particularly, in a multi-slice X-ray CT apparatus that uses a plurality of rows of detectors for detecting an X-ray image formed by helical scanning of the surrounding of a subject to be examined, this invention relates to a technique for achieving a data interpolation and an image reconstruction based on data by helical scanning of the subject by tilting a patient couch or a gantry.

2. Description of the Background Art

There have so far been proposed X-ray CT apparatuses using a helical scanning system. The X-ray CT apparatus based on the helical scanning system collects tomographic image data of a subject to be examined 12 by moving a patient couch to a body axial direction (hereinafter to be referred to as a Z-axial direction) of the subject 12 in synchronism with a continuous rotation of both an X-ray focus 13 and a detector 11, as shown in FIG. 1. In other words, in the helical scanning system, X-ray CT apparatus moves the patient couch to a body axial direction of the subject 12 through a center of the rotation of the X-ray focus 13 and the detector 11 while rotating these units. Accordingly, it can be understood that the X-ray focus 13 and the detector 11 take a spiral locus around the subject 12. On the other hand, FIG. 2 is a view for explaining a conventional scanning system for collecting data by moving the patient couch for each rotation of the X-ray focus and the detector. As compared with the conventional scanning system, the helical scanning system achieves a scanning at a higher speed over a wider range.

The X-ray CT apparatus based on the helical scanning system is further broadly divided into two kinds, that is, a single-slice CT apparatus and a multi-slice CT apparatus, based on a structure of the detector.

The first single-slice CT apparatus has an X-ray beam generation source for irradiating fan-shaped X-ray beams (hereinafter to be referred to as fan beams), and a detector having M channels (for example 1,000 channels) arrayed in a fan shape or in a linear shape in one row. This single-slice CT apparatus has the X-ray beam generation source and the detector rotated around the subject, and collects M data (for example of 1,000 data) in one rotation. Data collection in one time is called one view.

The second multi-slice CT apparatus has an X-ray beam generation source for irradiating conical X-ray beams (hereinafter to be referred to as cone beams), and a two-dimensional detector having detectors arrayed in a Z-axis (body axis) direction in a plurality of rows, each detector having an arcuate array of M-channel detectors (M channels times N rows). FIGS. 3A, 3B and 3C show detectors, each detector having two rows, four rows and eight rows, respectively. The multi-slice CT apparatus rotates the X-ray beam generation source (X-ray focus) 13 and the detector 32 around the subject, and collects M times N data in one rotation. Accordingly, as compared with the first single-slice CT apparatus, it is possible to scan over a wide range in higher precision and at a higher speed.

In the coordinates of scanning in FIG. 4, the Z-axis (body axial direction) coincides with a slice direction in which the slicing proceeds.

FIG. 5 is a view for showing the scanning of the multi-slice CT apparatus as observed from a Z-axial direction. In the drawing, a reference numeral 51 within a circle represents an effective field of view diameter FOV (Field of View). A reference numeral 52 placed between the X-ray focus 13 and the center of the FOV represents a distance between the X-ray focus and the rotation center, FCD (Focus Rotation Center Distance). A reference numeral 53 represents a fan angle. FIG. 6 is a view of a four-row multi-slice CT as observed from a direction perpendicular to the Z-axis including the Z-axis. A beam thickness 61 in the Z-axial direction, when X-rays incident from the X-ray focus 13 to the detector element 32 has passed through the rotation center (that is, FCD 52), is expressed as a reference slice thickness T. In FIG. 6, a central slice exists between the second-row detector and the third-row detector. A couch travel distance in one rotation is called a helical pitch. A helical pitch P (as represented by 62) in the multi-slice CT becomes a product of the number of detector rows N times the reference slice thickness T.

Next, an outline of an image reconstruction processing in the helical scanning system will be explained. In the following explanation, the subject 12 having only an arrow signal around the rotation is considered as shown in FIG. 7.

(1) Projection Data Collection Processing

First, as shown in FIG. 8A, projection data collected by the detector at each view of the helical scanning is collected for all angles. The projection data is corrected by taking into consideration the sensitivity of the detector, the X-ray intensity and various other physical factors. The data after the correction is called raw data.

(2) Helical Interpolation Processing

Second, in the case of the helical scanning, interpolation is conducted based on the raw data in a Z-axial direction, to generate interpolated data on a desired slice surface. This interpolation is called a helical interpolation. This processing is carried out, as only data of one view is collected on the targeted slice surface according to the helical scanning. The interpolation processing will be explained in detail later.

(3) Convolution Processing

Third, as shown in FIG. 8B, the interpolated data for the respective angles are subjected to convolution calculation of a reconstructing function (a filter function). FIGS. 10A, 10B, 10C and 10D show examples of shapes of filters. These filter shapes are selected according to the characteristics of the image data to be obtained. The convoluted data after the calculation exhibits a shape with a decay on the surrounding for an actually existing signal.

(4) Back Projection and Fan Beam Reconstruction Processing

Fourth, the convoluted data is added to all the pixels which are arrayed along the path of an X-ray beam at the time of data collection. FIG. 9 shows a result of the back projection calculation at a certain angle. When this back projection is repeated for the convoluted data at necessary angles according to the beam shape, only the original signal remains, and desired image data is fan-beam reconstructed.

An interpolation method in the case of carrying out a helical scanning in the multi-slice CT apparatus will be explained next. As such an interpolation method, there exists an adjacent interpolation method as disclosed in Japanese Laid-open Publication Hei 4-224736. FIG. 15 shows a conceptional diagram of the adjacent interpolation method for the case where the helical pitch is 4 in the four-row multi-slice CT. According to this adjacent interpolation method, real data or opposite data corresponding to the real data at two adjacent points in a Z-axial direction (slice direction) at a target slicing position, are used for linear interpolation with an inverse ratio of a distance between the target slicing location 151 and the sampling position. In this case, the real data is equivalent to the raw data. This adjacent interpolation method is a method employed by extensively applying a 360-degree interpolation method used for the single-slice CT apparatus. As shown in FIG. 11, according to the 360-degree interpolation method, real data 152 and 153 of two views which are in same phase with each other at the nearest positions and sandwiching a target slice plane 151, are used for linear interpolation with an inverse ratio of a distance between the slice plane and the sampling position. This processing is repeated for all the necessary phases.

Further, in Japanese Laid-open Publication Hei 9-234195, there is disclosed a filter interpolation method for performing an addition of weighted multi-point data. FIG. 16 shows a conceptional view of the filter interpolation method. According to this filter interpolation method, real data group and/or opposite data group opposite to the real data group are filtered (added with weight) in the Z-axial direction (slice direction), thereby obtaining data of a target slicing position 151.

Further, an opposite beam interpolation method which is used in the single-slice CT apparatus can also be used. According to this opposite beam interpolation method, opposite data are formed which are virtual data based on opposite beams shown by broken lines in FIG. 12 extracted from each focal position. This is a two-point interpolation method for linearly interpolating between the opposite data and the real data as shown in FIG. 13. FIG. 14 is a view for explaining a sampling position of an opposite beam. In the above-described Japanese Laid-open Publication Hei 9-234195, a new opposite beam interpolation method which is an extended application of this opposite beam interpolation method is disclosed. FIG. 17 and FIG. 18 show conceptional views of the new opposite beam interpolation method. According to this new opposite beam interpolation method, interpolated data of a target slice is obtained by interpolating between the two nearest beams by sandwiching a slice surface from all the beams regardless of the opposite data or the real data. A shaded area in FIG. 15 shows one example of a data sampling range according to the adjacent interpolation method using the real data in the multi-slice CT. Shaded areas in FIG. 17 and FIG. 18 show one example of a data sampling range for the interpolation using the real data and the opposite data (new opposite beam interpolation method).

In the case of carrying out the helical scanning in the multi-slice CT apparatus, interpolated data is generated and image reconstruction is performed by using the above-described various helical scanning methods.

However, the conventional multi-slice CT apparatus has the following problems.

In the clinical operation, image reconstruction is usually performed by collecting data based on not only a scanning of a perpendicular slice surface but also based on a scanning of a tilted slice surface, not perpendicular to a body axial direction (couch moving direction), by tilting the gantry. This scanning is called a tilt scanning. A slice plane in the case of the tilt scanning is called a tilt plane.

Coordinate system of a tilt scanning will be defined by using FIG. 19. When a tilt angle of the gantry is set as a tilt angle α, a Z' axis is defined with a tilt of the tilt angle α with respect to the body axis (Z axis). In FIG. 19, the Z' axis is a travel direction of the slice, and this is defined as perpendicular to a gantry rotation plane 191 (that is, the tilt plane) including a tubular bulb and a detector. The X-axis is a straight line formed by crossing two slice planes before and after the tilt. The coordinate system is structured by Y'-axis perpendicular to the X-axis and the Z'-axis respectively, and Y-axis perpendicular to the X-axis and the Z-axis respectively. In FIG. 19, the couch moves in the Z-axial direction. On the other hand, the gantry travels in a Z'-axial direction by scanning the adjacent slices as shown by dotted lines. The coordinate system of FIG. 19 can be applied to arbitrarily desired tilt direction and tilt angle. As can be understood from the coordinate system in the tilt scanning shown in FIG. 19, the Z-axial direction does not coincide with the Z'-axial direction (slice direction), and a predetermined tilt angle α is formed.

However, the above-described various conventional helical interpolation methods can be applied to only the case where the body axial direction in which the couch moves and the slice plane forms a perpendicular angle. Accordingly, there is a problem that these interpolation methods cannot be applied when a helical scanning is carried out by tilting the gantry in the multi-slice CT.

The reasons are as follows. When a helical scanning is carried out by tilting the gantry by only the angle α in the multi-slice CT apparatus, the rotation center of each detector row of the couch is deviated to up and down directions, that is, in a Y'-axial direction or a Y-axial direction. This deviation will be explained based on FIG. 20. Fan beams 201 shown by thick lines in FIG. 20 are an X-ray focus and X-ray paths in an n-th rotation with respect to a detector in the first row. On the other hand, fan beams 202 shown by thin lines in FIG. 20 are an X-ray focus and X-ray paths in an n-th rotation with respect to a detector in the second row. As can be easily understood from FIG. 20, the X-ray paths of the detector rows for the same channel are deviated (deviated to a moving direction of the couch) when observed from a Z-axial direction. Therefore, according to the data collected based on the X-ray beams irradiated from such different focal positions, the X-ray paths extending in a fan shape are deviated.

In this case, a deviation to a Y'-axial direction (Shift Y' (n)) and a deviation to a Y-axial direction (Shift Y(n)) from the central slice (midplane) shown in FIG. 6 are given by the following Expression 1 and Expression 2, respectively.

$$\text{Shift Y'(slice, } n, a) = Zt(\text{slice, } n) \times \tan(\alpha) = \\ \text{slice} \times (Nc-n) \times \tan(\alpha) \quad \text{(Expression 1)}$$

$$\text{Shift Y(slice, } n, a) = Zt(\text{slice, } n) \times \sin(\alpha) = \\ \text{slice} \times (Nc-n) \times \sin(\alpha) \quad \text{(Expression 2)}$$

where N represents a number of rows of collection, Slice represents a thickness of slice in each row, Nc represents a central slice of equal Z'-axis coordinates to X-ray focus, and Zt (n) represents a distance from the central slice to each slice on the Z'-axis coordinate.

In the above-described helical interpolation, it is necessary to interpolate between the data each having the same constant distance from a certain pixel to a focus, in order to obtain reconstructed image data with practical picture quality having eliminated any blurs. For this purpose, the two data between which the interpolation is carried out need to be the data on the same path coming from the same focus, when observed from the Z'-axial direction in which the interpolation is carried out. In other words, it is necessary to use the data having no deviation in the X-Y' direction and being deviated in only the Z'-axial direction, as the base data for interpolation.

However, when the above-described tilting of the gantry is carried out, the collected data of respective rows serving as two-point or multi-point real data groups (or real data and opposite data) for generating the interpolated data, have their X-ray focus and X-ray paths deviated in a X-Y' plane direction. In other words, the data of an identical view angle and an identical ray angle (that is, channel angle) as those of the other data between which the interpolation is to be carried out, is deviated in the X-Y' plane direction. Therefore, there is no data between which the interpolation can be performed.

Also, in the case of the above-described single-slice CT apparatus, the gantry rotation plane and the couch moving direction including the tubular bulb and the detector are not perpendicular to each other because of the tilting of the gantry. However, as only one detector row exists in the single-slice CT apparatus, there occurs no deviation in the X-ray paths. Accordingly, in the case of the single-slice CT, it is possible to carry out the image reconstruction based on the usual fan-beam direct back projection method or the like, by helically interpolating between the data of an identical view angle and an identical channel angle (that is, a ray angle) while disregarding a tilt of the tilt angle α.

As explained above, when a helical scanning is carried out in the multi-slice CT apparatus, it has not been possible to perform an image reconstruction based on a method of helical interpolation and image reconstruction in the multi-slice CT apparatus as shown in FIG. 15 to FIG. 18, such as, for example, the method as described above for performing a helical interpolation by taking out data for one rotation, and performing a filtered back projection based on the fan beam direct back projection method. Therefore, it has not been possible to implement a helical scanning by tilting the gantry in the multi-slice CT apparatus.

SUMMARY OF THE INVENTION

The present invention has been developed in order to solve the above-described problem that it is not possible to perform a helical interpolation when it is desired to carry out a helical scanning by tilting a gantry in a multi-slice CT apparatus, as there occurs a deviation in the X-ray path in each row of a detector.

It is an object of the present invention to provide an X-ray CT apparatus capable of realizing an image reconstruction based on a helical scanning by tilting a gantry in a multi-slice CT apparatus.

An aspect of the present invention is in that data collected based on fan beams are converted into data of parallel beams (this processing will hereinafter be referred to as a fan beam data-parallel beam data conversion), thereby eliminating a focus, and that the data after converted into parallel beam data are subjected to a positional correction based on a tilt amount.

According to one aspect of the present invention, as shown in FIG. 21, there is provided an X-ray computed tomography apparatus, comprising: a couch on which a subject to be examined is to be placed; a gantry, including an X-ray source for generating X-rays, and a detector having detector elements laid out in a plurality of rows in a slice direction for detecting X-ray beams transmitted through the subject; a data collector for collecting helical data by the detector, by rotating the X-ray source while moving at least one of the gantry and the couch along a body axial direction of the subject in a state that at least one of the gantry and the couch is tilted; and a data processor for reconstructing an image by interpolating between the helical data collected by the data collector.

The data processor may interpolate between the helical data based on a tilt angle of the couch or the gantry. The data processor may interpolate between the helical data in a slice direction or in a body axial direction.

According to the above-described structure, in a multi-slice CT apparatus, it becomes possible to collect projection data by carrying out a tilt helical scanning, and reconstruct an image by a helical interpolation based on the collected projection data and tilt data. In other words, in the multi-slice CT apparatus, it becomes possible to carry out a helical scanning capable of collecting data over a wide range at a high speed by tilting the gantry or the couch.

Further, the data processor may include: a data converter for converting helical data collected by the data collector into parallel beam data; and a shift data calculator for calculating shift data that corrects a deviation of X-ray paths generated by the tilting of the couch or the gantry.

When the fan beam data-parallel beam data conversion is used, the data collected by the helical scanning (herein after referred to as helical data) are converted into the parallel beam data so that a focus of the X-ray paths is eliminated. Thus, it is possible to carry out a helical interpolation by easily correcting positions of the collected data of each row of the detector on the X-Y' plane.

The data converter converts fan beam data of each view angle into the parallel beam data by selecting each X-ray path data that is parallel with the reference path. Thus, it becomes possible to easily generate the parallel beam data at a high speed from the collected data, and to select data for interpolation.

With the above-described structure, it becomes possible to easily calculate a positional correction amount of the data collected for each row of the detector on the X-Y' plane and to obtain reconstructed image data at a high speed and in high picture quality.

Further, with the above-described structure, it becomes possible to apply various helical interpolation methods by suitably selecting data, without being conscious that the data is helical scan data obtained by tilting the gantry.

As a helical interpolation method, it is possible to use so-called a filter interpolation method for obtaining interpolated data by adding weighted multi-point sampled data.

Further, with the above-described structure, it becomes possible to obtain reconstructed image data of a small effective slice thickness and in high picture quality, by decreasing deterioration in the picture quality due to a change-over of beams that are used for the interpolation.

The correction based on the shift data may be carried out during a generation of parallel beams, or during a helical interpolation or during an image reconstruction.

According to the above-described structure, it is possible to carry out a helical interpolation by easily correcting on the X-Y' plane the positions of the parallel beam converted data collected for each row of the detector, and to obtain reconstructed image data at a high speed.

It is also possible to improve the parallel processing of the image reconstruction processing by carrying out a helical interpolation based on a conversion of data collected by helical scanning into parallel beam data and thus eliminating a focus of X-ray paths, and by generating reconstructed image data based on a positional correction of interpolated data for each view angle during a back projection processing.

The conversion of the helical data into the parallel beam data can be carried out by the data converter, and the data converter selects each X-ray path data that is parallel with the reference path, for each fan beam data at each view angle.

The shift data is obtained based on a tilt angle formed by the rotation plane of the gantry and a slice direction or a body axial direction perpendicular to the rotation plane. Further, the shift data is obtained based on at least one of the tilt angle, the slice thickness, the view angle, and the number of rows of the detector. Further, the shift data is obtained based on a relative distance between the central slice and each detector row.

The data processor may generate interpolated data by adding weighted multi-point sampled data.

The data processor may carry out convolution and back projection to each of data of identical view angle, and reconstruct an image by superimposing the projected data.

The data processor may further include a data corrector for correcting a deviation of slicing positions of the parallel beam data.

According to the above-described structure, it is possible to obtain a reconstructed image of higher picture quality by correcting the deviation of slicing positions of each parallel beam data.

Other features and advantages of the present invention will become apparent from the following description taken in conjunction with the accompanying drawings.

BRIEF DESCRIPTION OF THE DRAWINGS

The accompanying drawings, which are incorporated in and constitute a part of he specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

An embodiment of a multi-slice X-ray CT apparatus according to the present invention will be explained in detail below with reference to FIG. 21 to FIG. 32.

In a helical scanning of an object by tilting a gantry in a multi-slice CT apparatus, the present embodiment provides a function of reconstructing an image by suitably selecting data to be interpolated therebetween, based on a calculation of an effective X-ray path for each data on a reconstructed image by taking a tilt angle and others into consideration. An X-ray CT apparatus according to the present embodiment converts fan beams of collected data into parallel beams, and interpolates between the data in an Z'-axial direction by taking a tilt angle and others into consideration, for example, by a filter correction two-dimensional parallel back projection method. Thus, the apparatus provides a reconstructed image. In this case, the Z'-axial direction is defined as a direction perpendicular to a gantry rotational plane, that is, a tilt plane.

The X-ray CT apparatus according to the present embodiment is a multi-slice X-ray CT apparatus (multi-slice CT-apparatus) for carrying out a helical scanning of a subject to be examined placed on a couch along a body axial direction or in a predetermined tilted angle with respect to the body axial direction so that a plurality of detectors arrayed in rows detect an X-ray image formed by the scanning.

Figure 1:
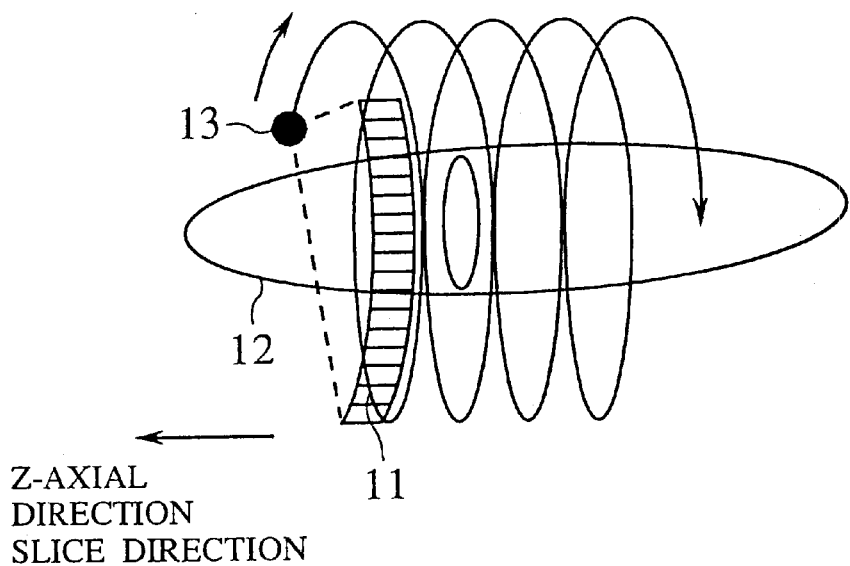
FIG. 1 is a view for explaining a helical scanning system in a conventional X-ray CT apparatus.
Figure 2:
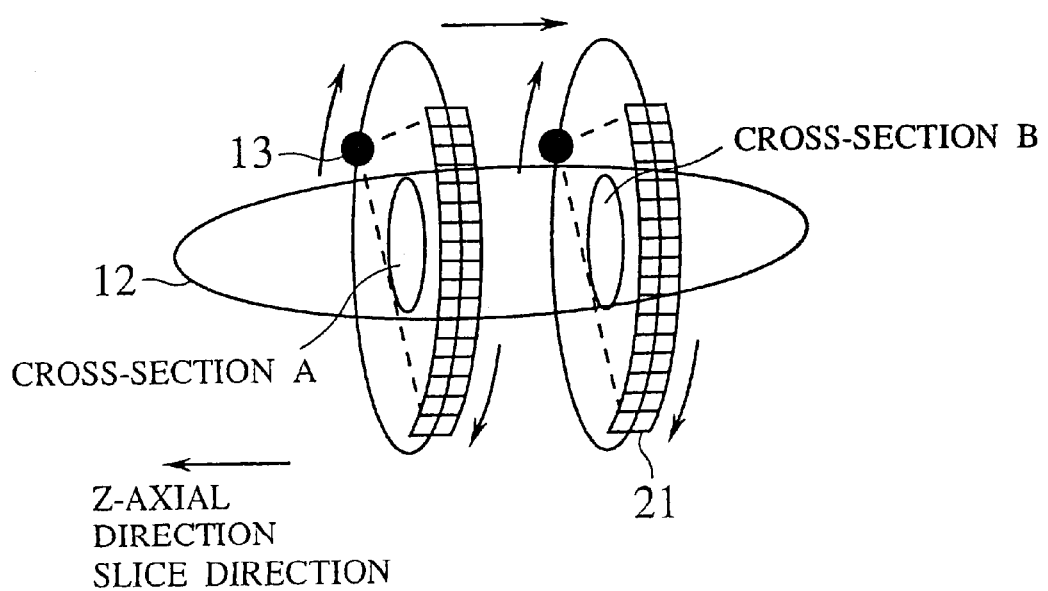
FIG. 2 is a view for explaining a conventional scanning system in an X-ray CT apparatus.
Figure 3C:
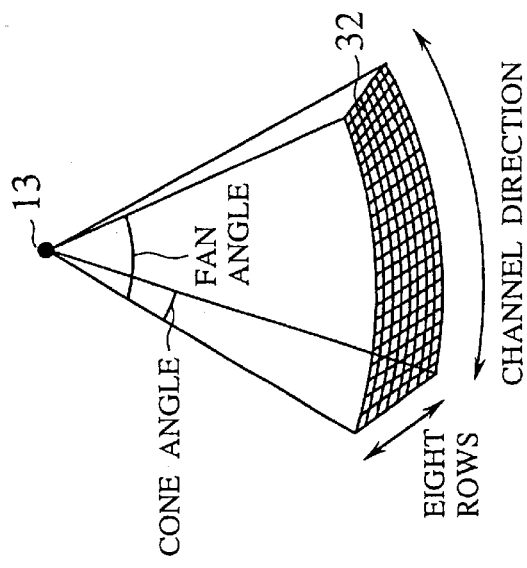
FIGS. 3A, 3B and 3C are views for explaining multi-slice apparatuses having detectors of two rows, four rows and eight rows, respectively.
Figure 3B:
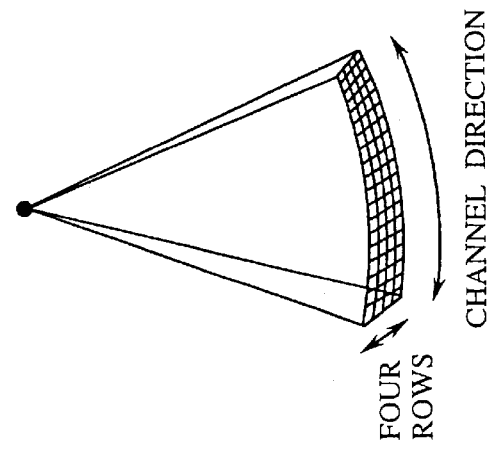
Figure 3A:
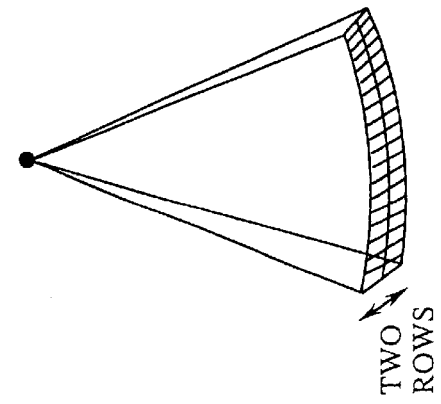
Figure 4:
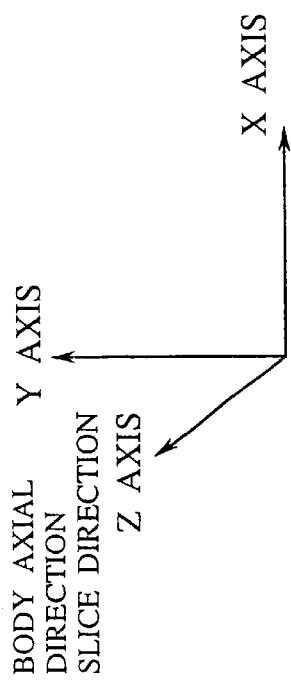
FIG. 4 is a view for explaining a coordinate system for a scanning.
Figure 5:
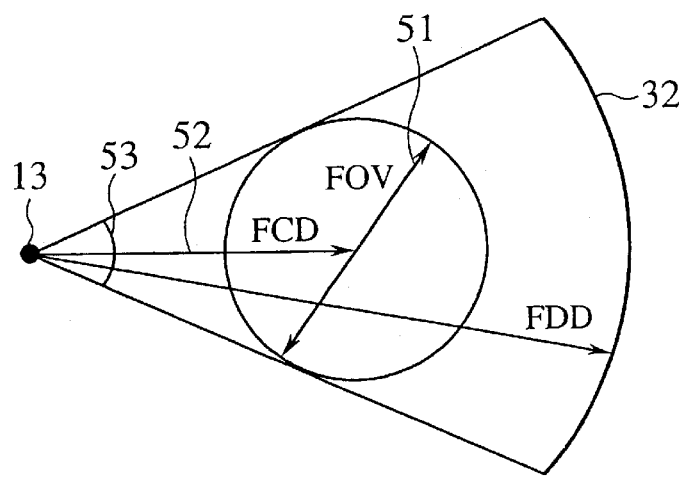
FIG. 5 is a diagram of X-ray beams in a multi-slice CT apparatus as observed from a Z-axial (body axial) direction.
Figure 6:
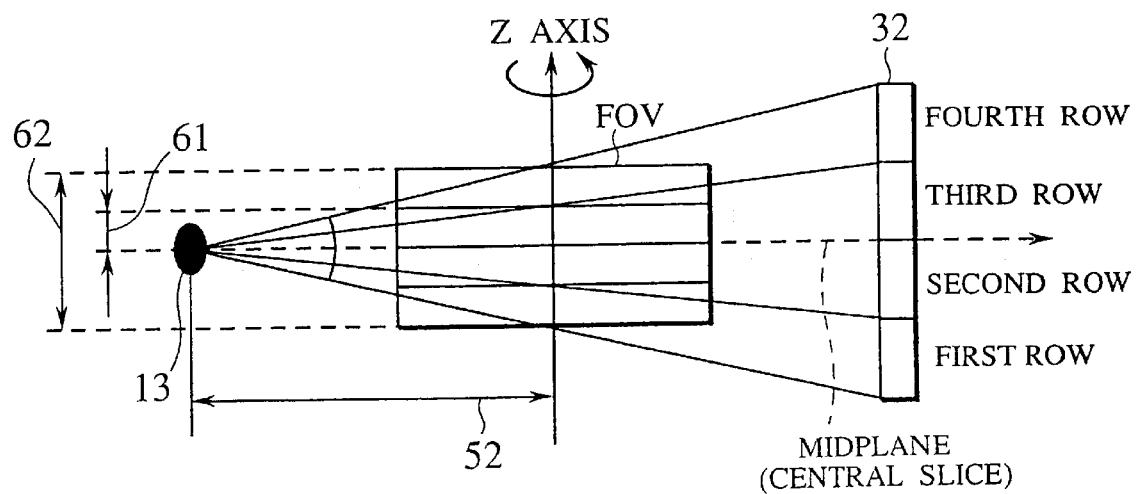
FIG. 6 is a diagram of X-ray beams in a multi-slice CT apparatus as observed from a direction perpendicular to the Z-axis.
Figure 7:
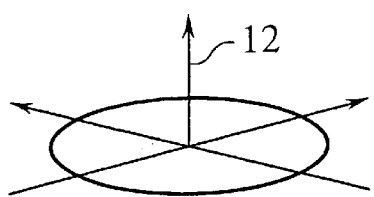
FIG. 7 is a view for explaining a subject to be examined in explaining an image reconstruction.
Figure 8A:
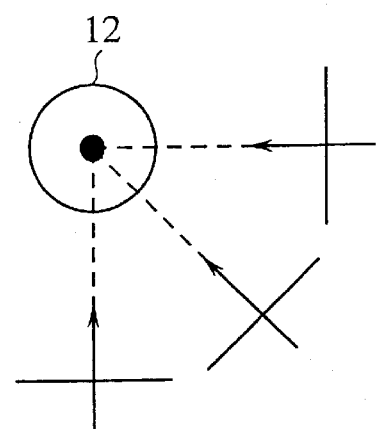
FIGS. 8A and 8B are views for explaining a projection data collection method and a back projection method in a helical scanning system.
Figure 8B:
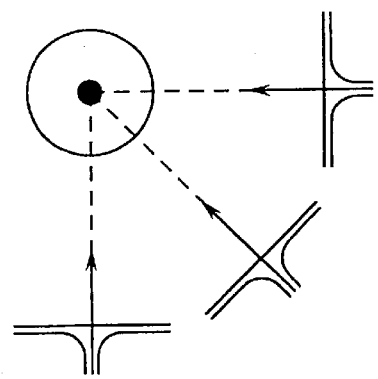
Figure 9:
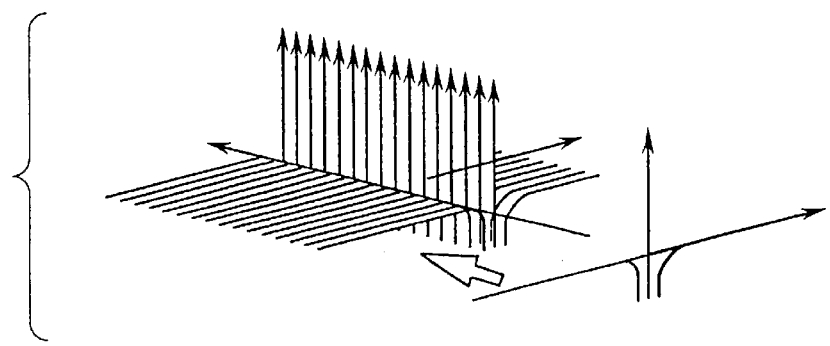
FIG. 9 is a view for explaining aback projection processing at a certain angle.
Figure 10A:
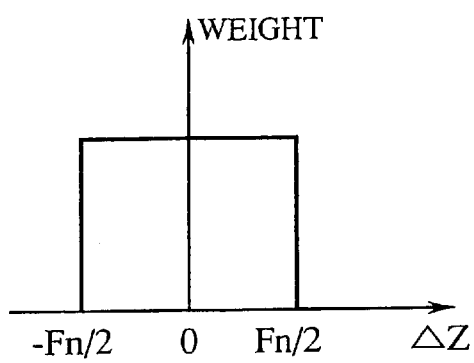
FIGS. 10A, 10B, 10C and 10D are views for showing examples of a filter function to be used for an image reconstruction.
Figure 10B:
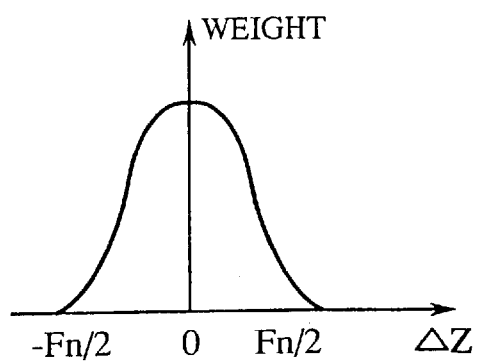
Figure 10C:
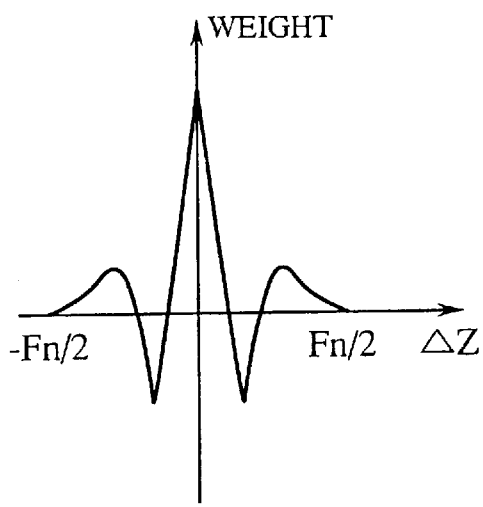
Figure 10D:
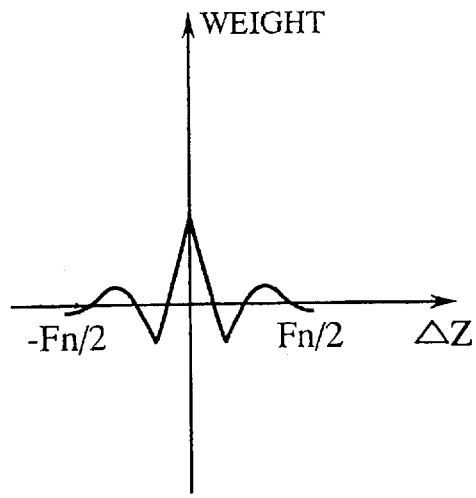
Figure 11:
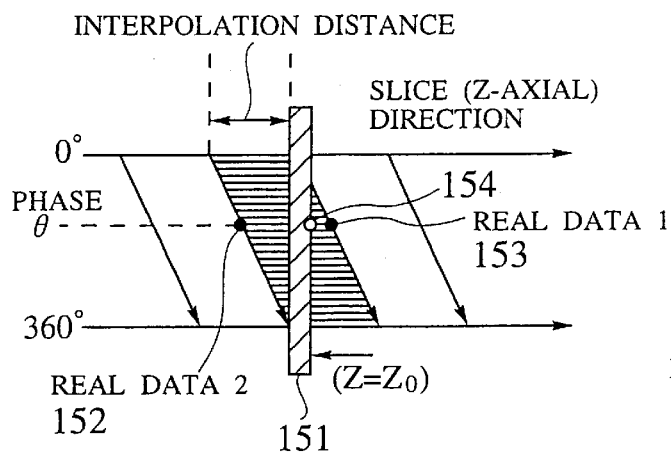
FIG. 11 is a conceptional view for explaining a 360-degree interpolation method in a single-slice CT apparatus.
Figure 12:
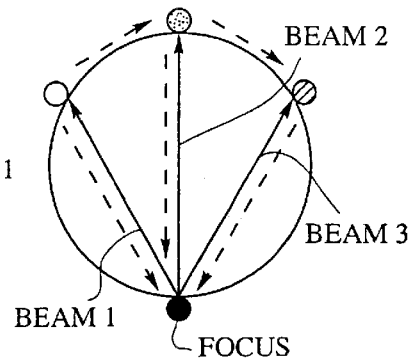
FIG. 12 is a view for explaining opposite beams in an opposite beam interpolation method.
Figure 13:
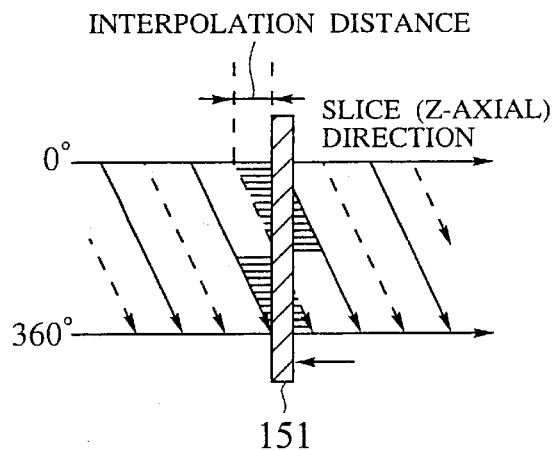
FIG. 13 is a conceptional view for explaining the opposite beam interpolation method.
Figure 14:
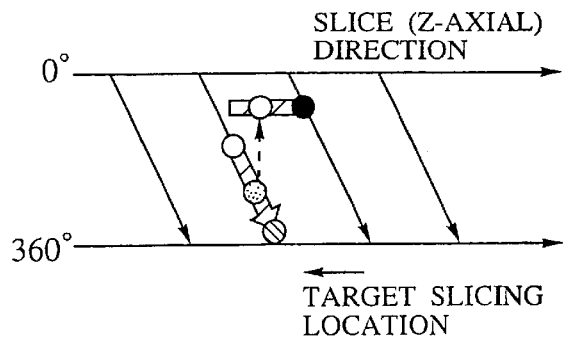
FIG. 14 is a view for explaining a sampling position of an opposite beam.
Figure 15:
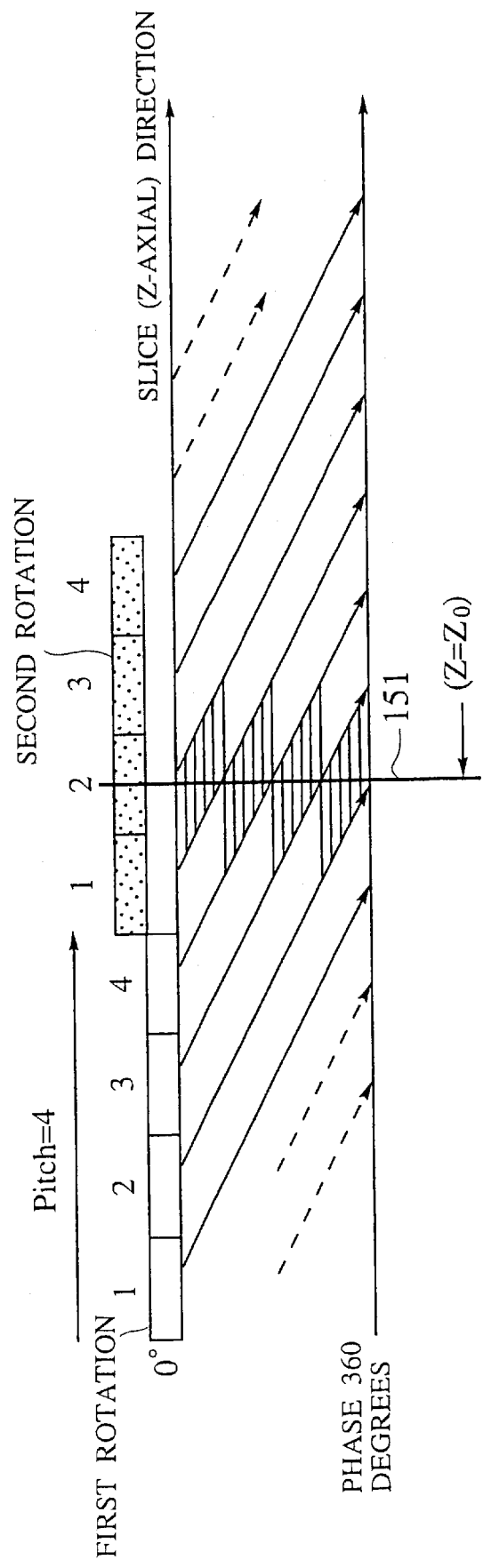
FIG. 15 is a conceptional view for explaining an adjacent interpolation method in the case where a helical pitch is four in a four-row multi-slice CT apparatus.
Figure 16:
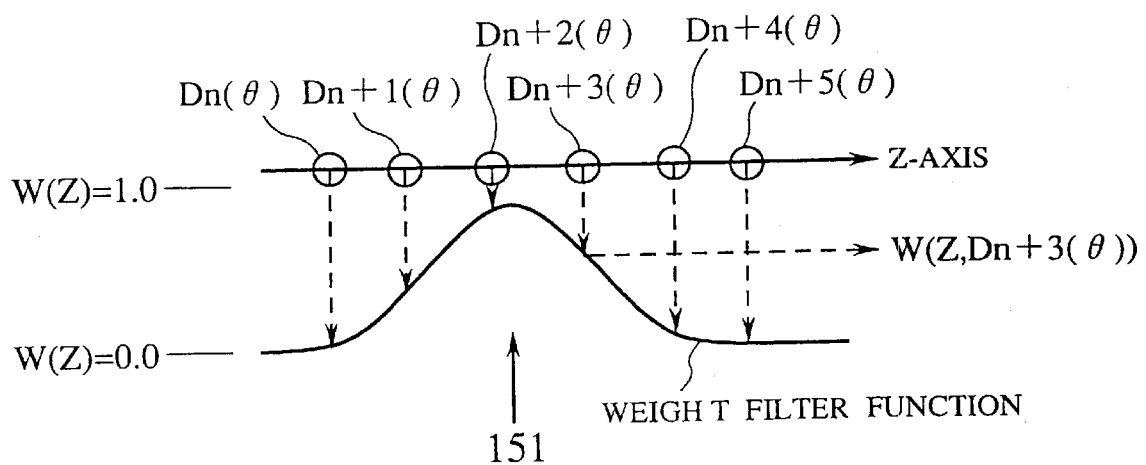
FIG. 16 is a conceptional view for explaining a filter interpolation method.
Figure 17:
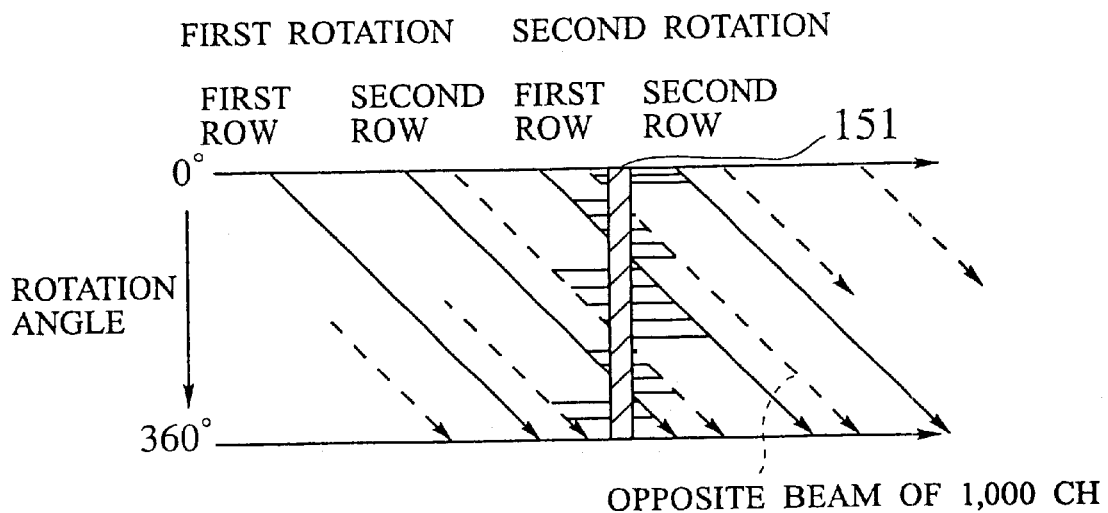
FIG. 17 is a view for explaining one example of a data sampling range in the adjacent interpolation method when real data is used in a multi-slice CT apparatus.
Figure 18:
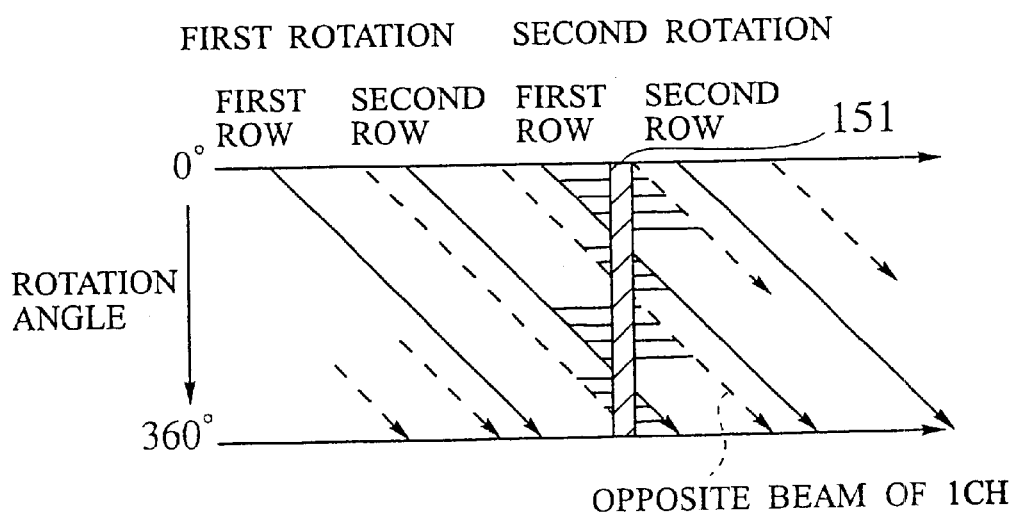
FIG. 18 is a view for explaining another example of a data sampling range in the adjacent interpolation method when real data is used in a multi-slice CT apparatus.
Figure 19:
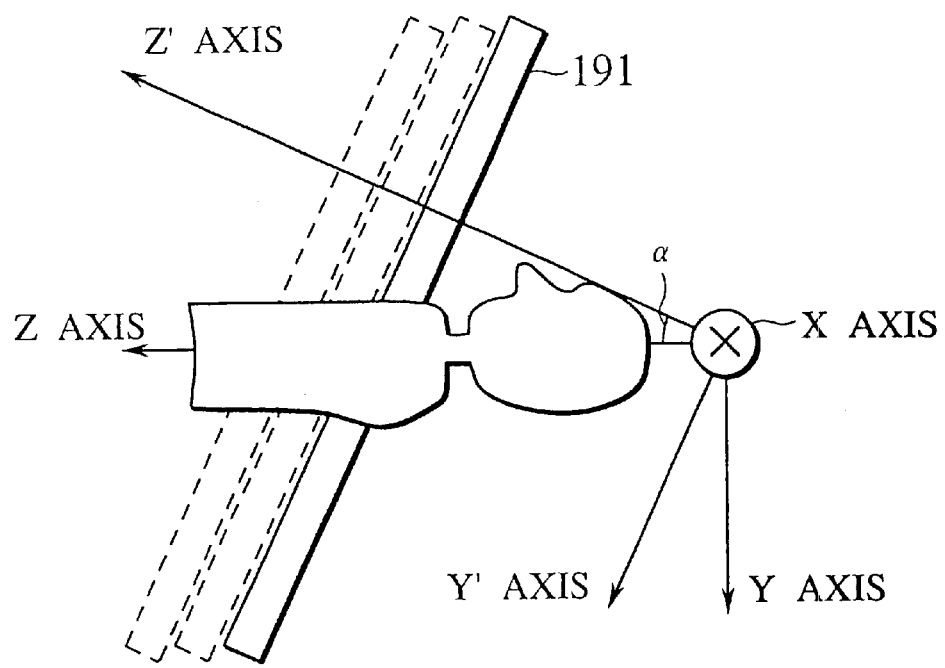
FIG. 19 is a view for explaining a coordinate system in a tilt scanning.
Figure 20:
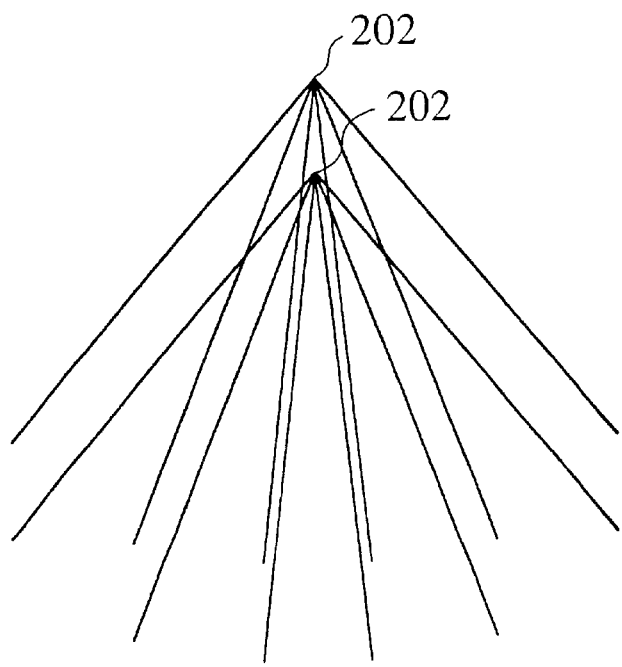
FIG. 20 is a view for explaining a deviation of X-ray paths generated by a plurality of detector rows in a helical tilt scanning.
Figure 21:
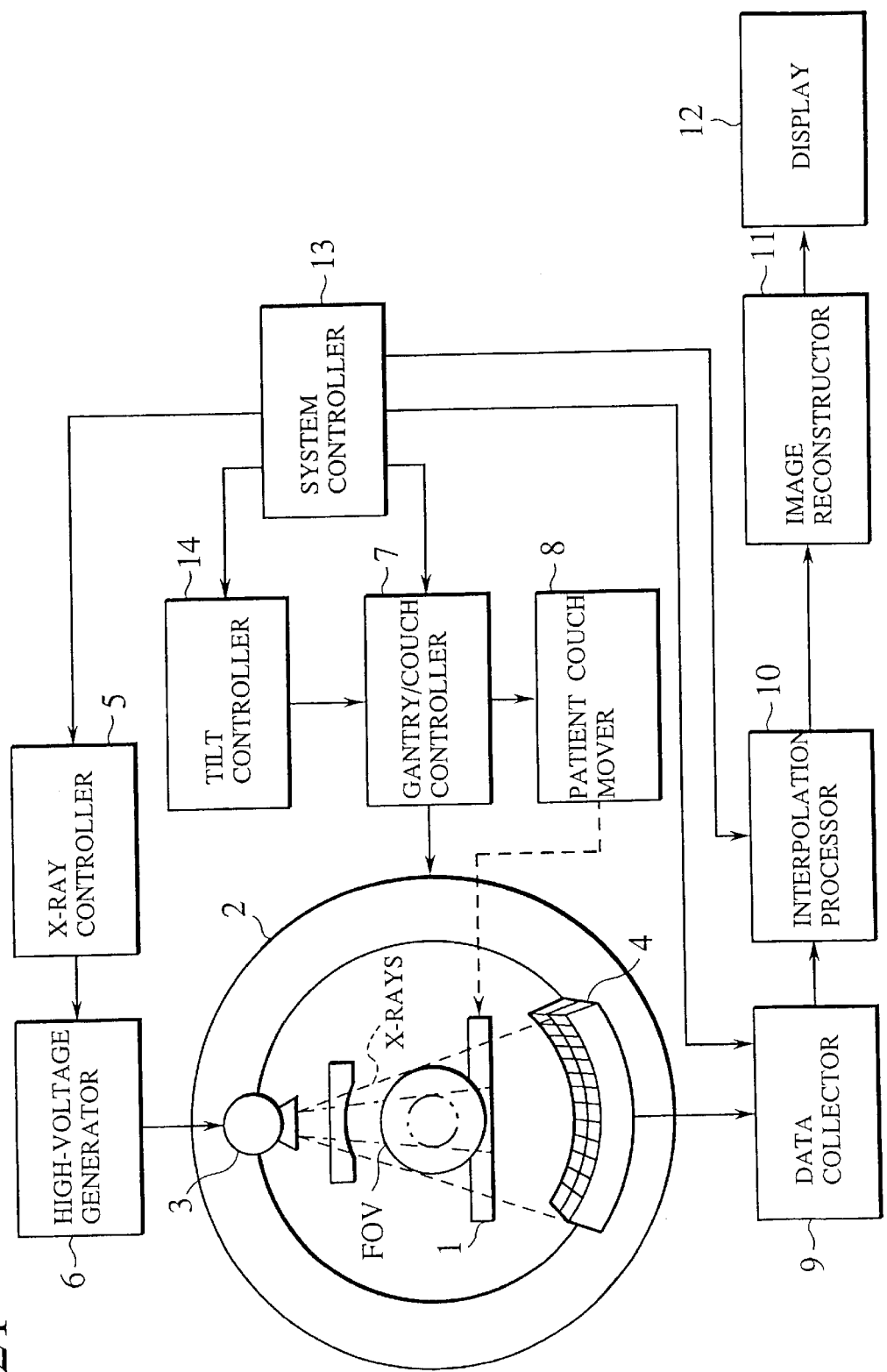
FIG. 21 a block diagram for showing a structure of an X-ray CT apparatus according to an embodiment of the present invention.

As shown in FIG. 21, the X-ray CT apparatus according to the embodiment of the present invention comprises a patient couch 1 on which a subject to be examined is placed, an X-ray tube 3 and an X-ray detector 4 rotatably and oppositely provided on the inner periphery of a gantry 2, an X-ray controller 5 and a high-voltage generator 6 for controlling the volume of X-rays irradiated from the X-ray tube 3, a gantry/couch controller 7 for controlling the move of the gantry and the couch in a rotational axial direction of the X-ray tube 3 and the X-ray detector 4 or by tilting the couch 1 by an optional angle from this rotational axial direction, and a couch mover 8.

The X-ray CT apparatus according to the embodiment of the present invention further comprises a data collector (i.e., data acquisition system: DAS) 9 for taking in and storing data detected by the X-ray detector, an interpolation processor 10 for carrying out a predetermined interpolation processing based on the data collected by the data collector 9, an image reconstructor 11 for reconstructing an X-ray image based on the interpolated data, a display 12 for displaying an X-ray image reconstructed by the image reconstructor 11, a system controller 13 for controlling the whole system of the multi-slice CT apparatus, and a tilt controller 14 for controlling a tilt amount of the couch.

The data collector (DAS) 9 corresponds to a data collector in claims of the present invention. The interpolation processor 10 and the image reconstructor 11 correspond to a data processor in claims.

The gantry 2 holds the X-ray tube 3 and the detector 4. The gantry 2 is rotated around a center axis passing through an intermediate point between the X-ray tube 3 and the detector 4 by a couch rotating mechanism not shown. The gantry 2 rotates in a desired tilt angle with respect to the couch 1 according to a tilt control signal sent from the gantry/couch controller 7.

The X-ray tube 3 irradiates X-ray beams at a high voltage supplied from the high-voltage generator 6.

The X-ray detector 4 is a multi-slice X-ray detector having detector rows laid out in N rows (for example, four rows) along the rotary axial direction, each detector row formed by having a plurality (for example, 1,000 channels) of X-ray detector elements laid out in a direction orthogonal (hereinafter to be referred to as a slice direction) with a rotary axial direction.

The X-ray controller 5 controls a timing of a generation of a high voltage by the high-voltage generator 6, based on an X-ray beam control signal output from the system controller 13.

The high-voltage generator 6 supplies a high voltage to the X-ray tube 3 for making the X-ray tube 3 irradiate X-ray beams, based on a control signal from the X-ray controller 5.

The gantry/couch controller 7 makes the gantry 2 rotate based on a gantry/couch control signal output from the system controller 13, and outputs a couch moving signal to the couch mover 8. Further, the gantry/couch controller 7 makes the gantry 2 to be tilted and rotated based on a tilt control signal from the tilt controller 14 according to a tilt request input from an input unit not shown.

The couch mover 8 obtains a move volume of the couch 1 in one rotation of the gantry 2 based on a couch moving signal output from the gantry/couch controller 7, and makes the couch 1 move based on this move amount.

The data collector (DAS) 9 collects X-ray beams detected by the detector 4 by relating the X-ray beams to a data collection control signal output from the system controller 13.

The interpolation processor 10 interpolates between X-ray beams at a target slicing position based on projection data of X-ray beams collected by the data collector 9. The fan beam data-parallel beam data conversion is carried out prior to the interpolation processing. A detailed structure of the interpolation processor 10 will be described later.

The image reconstructor 11 reconstructs an image based on X-ray beams interpolated by the interpolation processor 10.

The display 12 displays an image reconstructed by the image reconstructor 11 on a monitor not shown.

The system controller 13 outputs to the gantry/couch controller 7 a rotation speed, a slice thickness, a fan angle, etc. as a gantry/couch control signal among helical scanning conditions input from an input unit not shown. Further, the system controller 13 outputs to the tilt controller 14 a tilt control signal for controlling a tilt amount of the gantry 2. Further, the system controller 13 outputs an X-ray beam generation control signal to the X-ray controller 5. Further, the system controller 13 outputs to the data collector 9 a detection control signal for indicating a timing of detecting X-ray beams and a data collection control signal including various parameters for the data collection. Further, the system controller 13 outputs to the interpolation processor 10 an interpolation control signal including various parameters relating to the interpolation.

Next, a structure of the interpolation processor 10 will be explained in detail with reference to FIG. 22.

Figure 22:
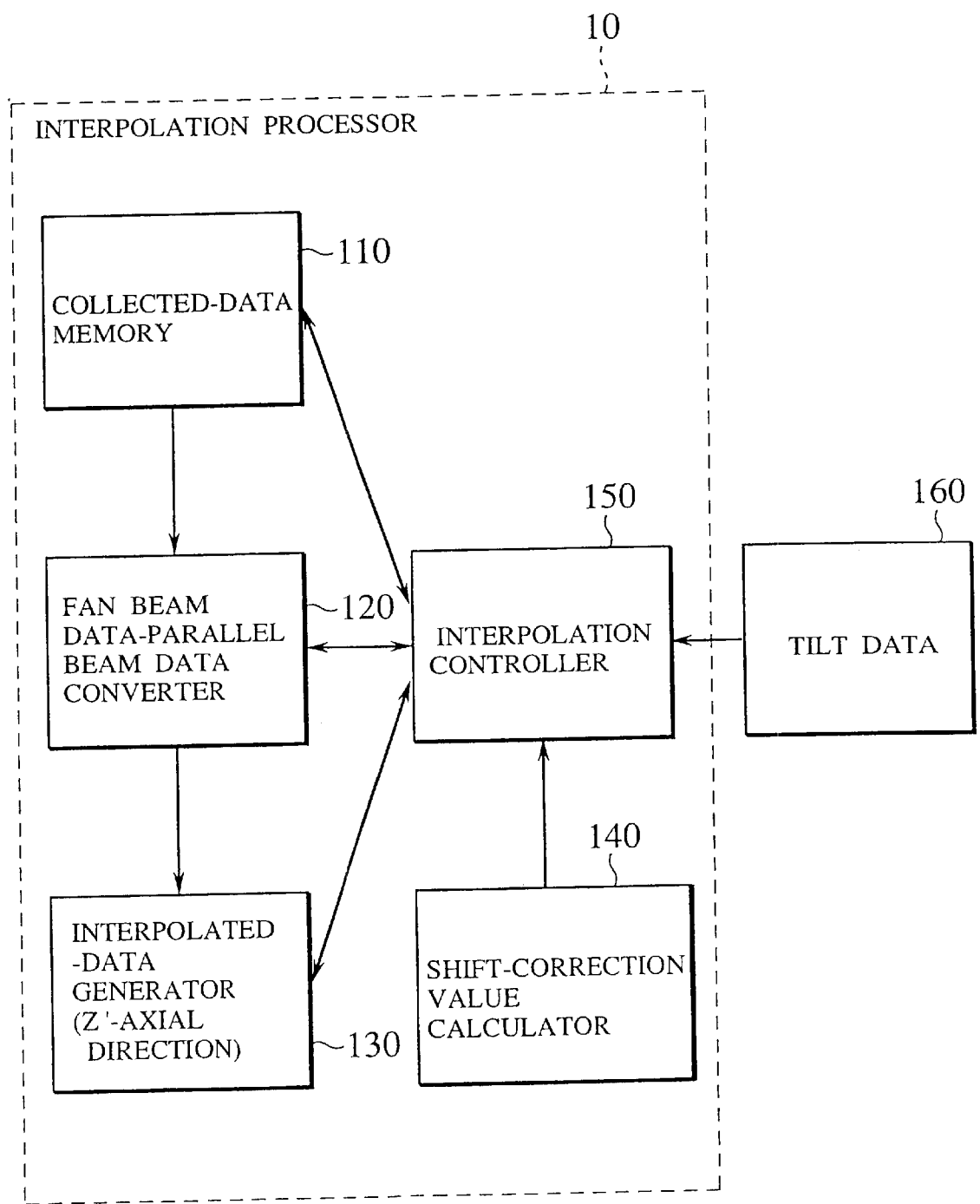
FIG. 22 is a block diagram for showing a detailed structure of an interpolation processor in FIG. 21.

As shown in FIG. 22, the interpolation processor 10 comprises a collected-data memory 110 for storing data collected by the data collector 9, a fan beam data-parallel beam data converter 120 for converting collected data of fan beam data into parallel beam data, an interpolated-data generator 130 for interpolating between the collected data converted into the parallel beam data in a Z'-axial direction at a target slicing position, a shift correction value calculator 140 for correcting a positional deviation volume of the parallel beam data in a channel direction (X-Y' direction), and an interpolation controller 150 for controlling the whole interpolation processing and for supplying a shift correction value calculated by the shift correction value calculator 140 to the fan beam data-parallel beam data converter 120, the interpolated-data generator 130, etc. based on tilt data 160 input from the system controller 13.

The operation of the X-ray CT apparatus of the present embodiment will be explained based on FIG. 23 to FIG. 32. At first, a principle of the image reconstruction processing of the present embodiment will be explained.

Figure 23A:
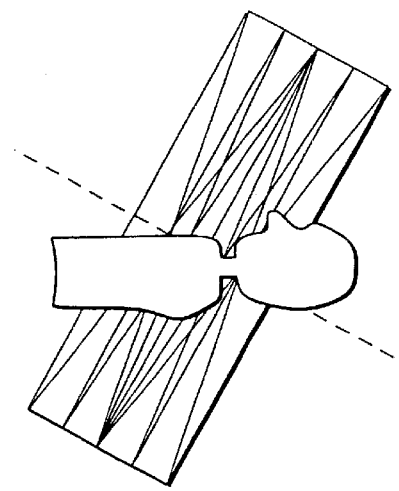
FIG. 23A and 23B are views for explaining a tilt scanning of a multi-slice CT apparatus according to the present embodiment.
Figure 23B:
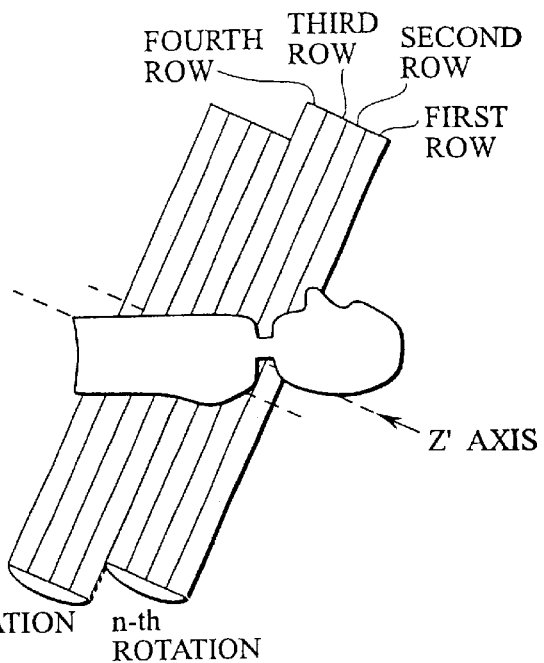

The X-ray CT apparatus of the present embodiment converts the collected data of helical scanning (FIG. 23A) into parallel beam data by the fan beam data-parallel beam data conversion, and hence eliminates a focus (FIG. 23B).

Figure 24:
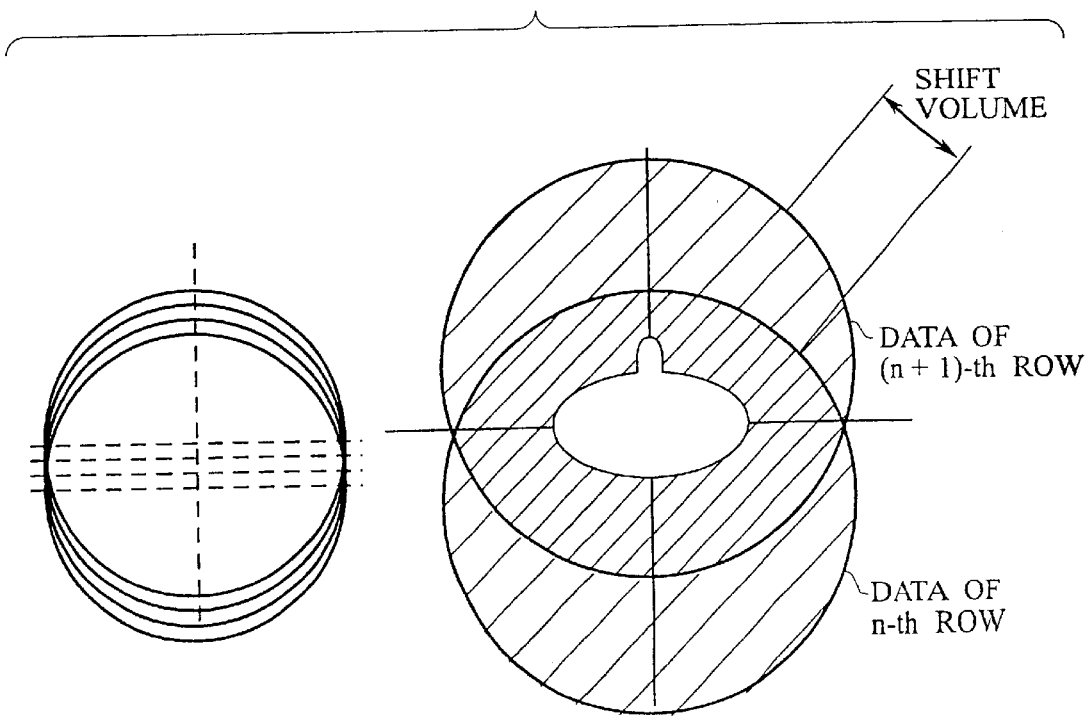
FIG. 24 is a view for explaining a shift amount to be used in a helical interpolation processing according to the present embodiment.

Then, the X-ray CT apparatus performs a positional correction to the post-converted parallel beam data to eliminate deviation in X-ray paths in each row, by taking into consideration a tilt angle, a view angle, a slice thickness and a relative distance between the central slice and the detector row (FIG. 24). This deviation in the X-ray paths is generated in a channel direction. In this case, as the collected data are converted into parallel beam data in the present embodiment, it can be understood that the parallel beam data should be shifted to a direction (a lateral direction) of a parallel beam projection axis (s-axis to be described later in FIG. 29). The parallel beam data are interpolated in a Z'-axial direction, and an image is reconstructed by the filter correction two-dimensional parallel back projection or the like. The Z'-axial direction is defined as a direction perpendicular to a tilt plane (a gantry rotational plane).

The image reconstruction operation of the X-ray CT apparatus according to the present embodiment will be explained in order.

(1) Data Collection Processing by Helical Scanning

At first, a helical scanning of the subject is carried out based on input helical scanning conditions. As the helical scanning conditions, there are input a number of detector rows, a number of detector channels, a thickness of each detector row at the rotation center in a Z-axial direction, FCD (focus to rotation center distance), FDD (focus to detector distance), FOV (effective field of view), an effective field of view angle (fan angle), a tilt angle, etc.

When the helical scanning conditions have been input, the system controller 13 outputs to the gantry/couch controller 7 a rotation speed, a slice thickness, a fan angle, etc. out of the helical scanning conditions as a gantry/couch control signal. At the same time, the system controller 13 outputs tilt data such as a tilt angle to the tilt controller 14. The gantry/couch controller 7 outputs a couch-moving signal to the couch mover 8 based on this gantry/couch control signal. At the same time, the gantry/couch controller 7 outputs to the gantry 2 a tilt control signal to the couch 1, based on a tilt control signal from the tilt controller 14.

When an operator has input a diagnosis starting instruction from the input unit in this state, the system controller 3 instructs the gantry/couch controller 7 to start diagnosing, and outputs to the X-ray controller 5 an X-ray beam generation control signal for controlling a generation of X-ray beams. In accordance with this X-ray beam generation control signal, the X-ray controller 5 makes the high-voltage generator 6 generate a high voltage. Based on the high voltage generated, X-ray beams are irradiated from the X-ray tube 3. Then, the couch 1 is moved by the couch mover 8, and a diagnosis is started by helical scanning.

In carrying out the helical scanning, the system controller 13 outputs a data collection control signal to the data collector 9. The data collector 9 collects X-ray beams from the detector 4 according to the data collection control signal, and supplies the collected X-ray beams (projection data, in actual practice) to the interpolation processor 10.

(2) Fan Beam Data-parallel Beam Data Conversion Processing

The interpolation processor 10 stores and holds X-ray beam data supplied from the data collector 9 in the data memory 110 according to a need. Next, the interpolation processor 10 converts the X-ray beam data into parallel beam data by the fan beam data-parallel beam data conversion.

A general procedure of the fan beam data-parallel beam data conversion will be explained next. This fan beam data-parallel beam data conversion is a method generally known. This method is generally used according to a need of image reconstruction processing, as it is possible to decrease the load of the interpolation and image reconstruction processing by converting the fan beams into parallel beams.

In the fan beam data-parallel beam data conversion carried out by the fan beam data-parallel beam data converter 120, X-ray paths that are parallel with a base X-ray path are selected one by one for each view angle. Alternatively, paths that are approximately parallel with the reference path are interpolated to generate parallel paths.

There will be shown below one example of an expression of a fan beam data-parallel beam data conversion for selecting data of parallel paths. In the following, a channel angle (ray angle) is represented by $\gamma$ (ch), a view angle is represented by $\beta$ (pview), and an axis perpendicular to parallel beams corresponding to each channel is represented by s-axis. Also, a maximum channel angle is represented by $\gamma m$. The parallel beams are expressed on the $\beta$–s coordinates.

Figure 25:
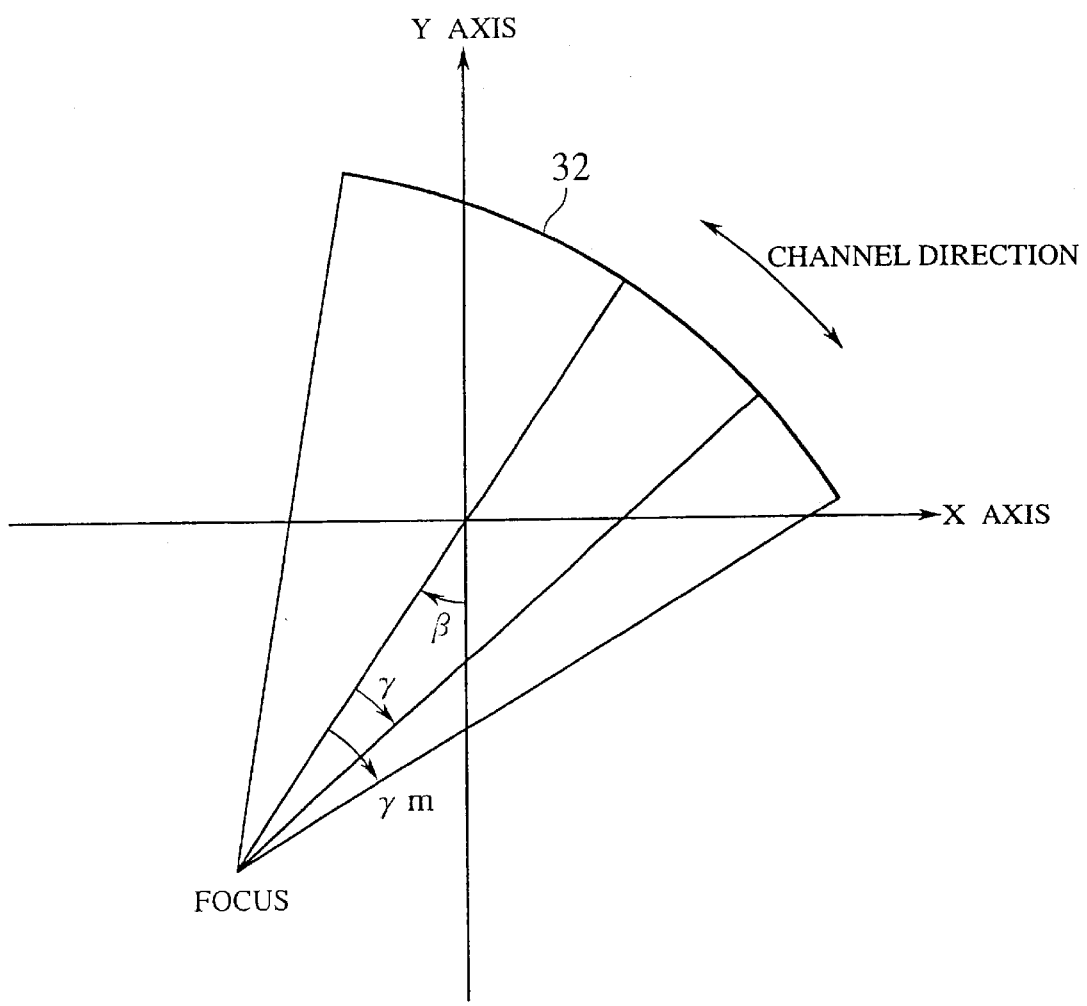
FIG. 25 is a view for explaining a geometric plane of a helical scanning on X-Y axis.
Figure 26:
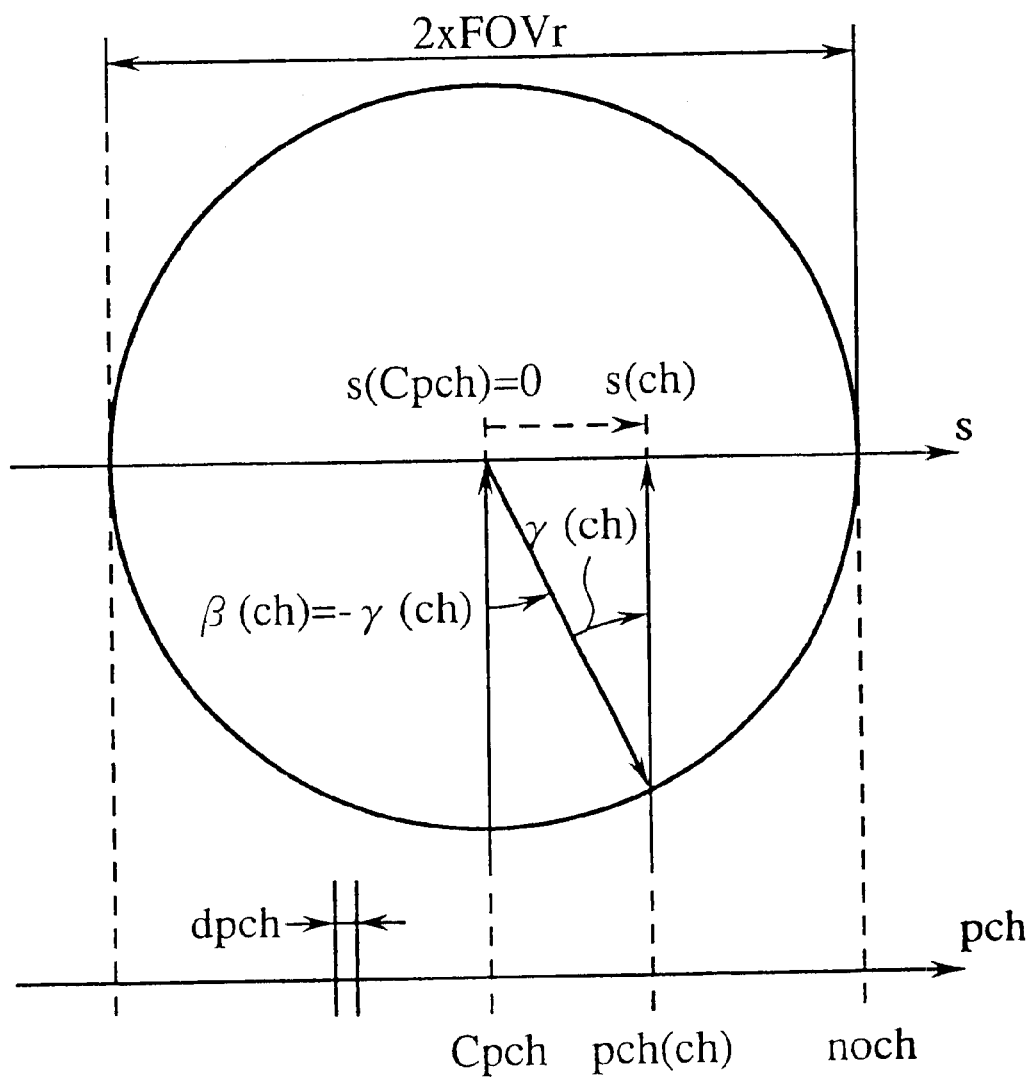
FIG. 26 is a view for explaining a geometric space in a fan beam data-parallel beam data conversion according to the present embodiment.

FIG. 25 shows a relationship between the channel angle (ray angle) $\gamma$ and the view angle $\beta$ of a geometry on the X-Y plane. FIG. 26 shows a geometry in the fan beam data-parallel beam data conversion. In the drawings, FOVr represents a radius of maximum field of view, CPch represents a central channel number in parallel beam data, and npch represents a number of channels in parallel beam data.

Figure 28:
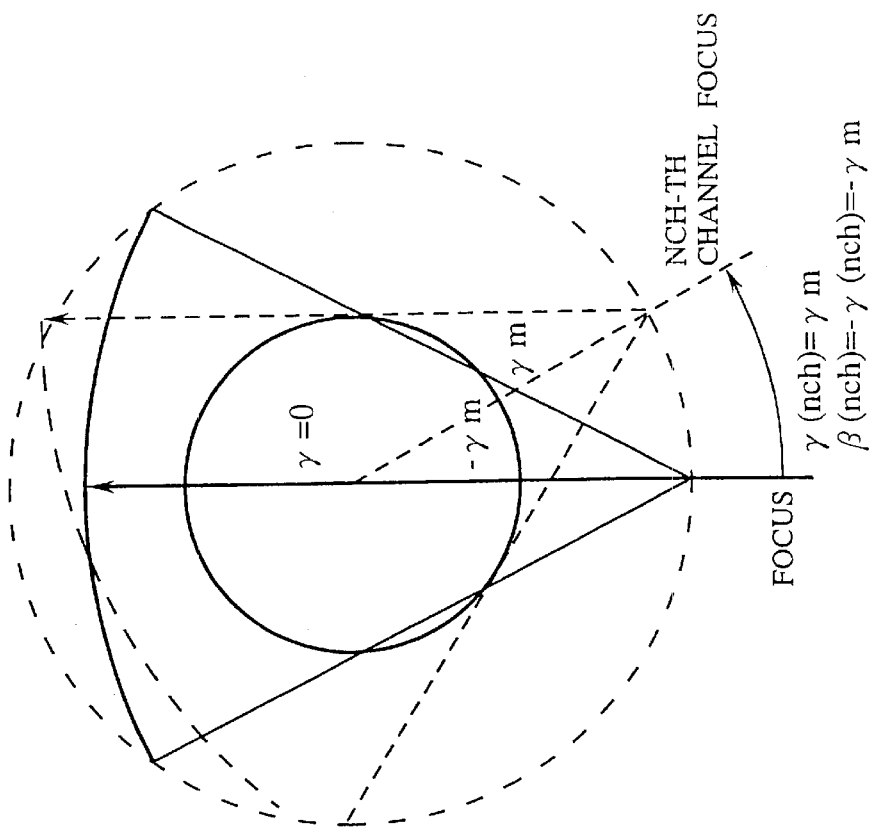
FIG. 28 is a view for explaining a method of selecting parallel beams at each view angle in a fan beam data-parallel beam data conversion.
Figure 27:
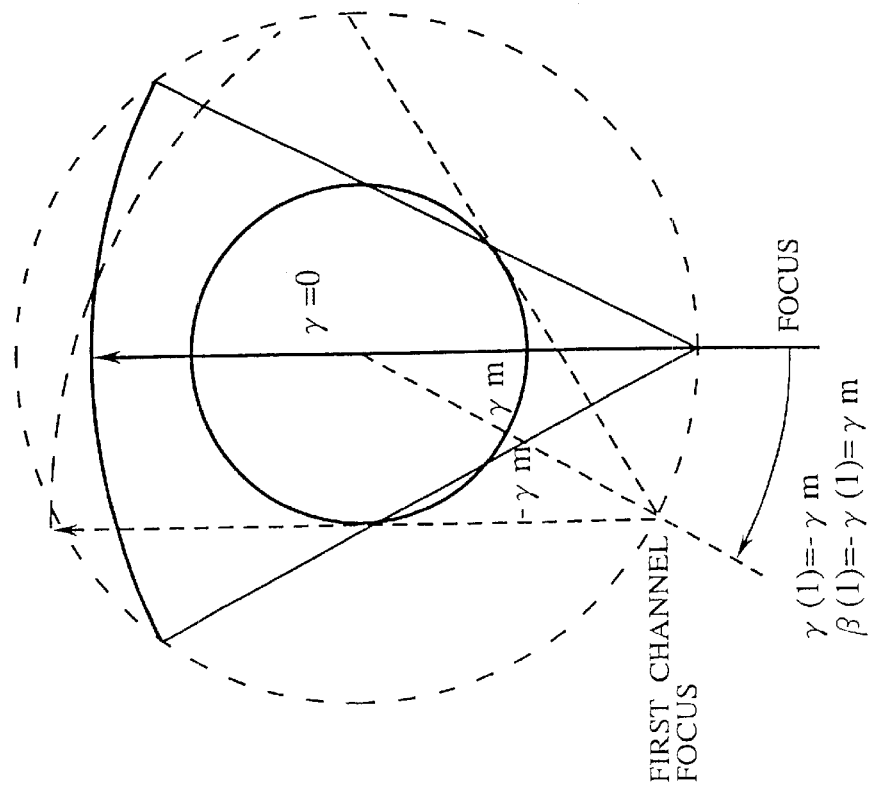
FIG. 27 is a view for explaining a method of selecting parallel beams at each view angle in a fan beam data-parallel beam data conversion.

FIG. 27 and FIG. 28 are views for explaining the concept of a selection of parallel beams at each view angle in the fan beam data-parallel beam data conversion.

As shown in FIG. 27, when a path passing through a rotation center from a base focus is expressed by a solid line arrow, and when the focus becomes a focus of an X-ray beam of a first channel, a beam expressed by a broken-line arrow (a path of a channel angle $\gamma=-\gamma m$ and a view angle $\beta=\gamma m$) is selected as a path parallel with the reference path (a path of $\gamma=0$) from out of the fan beams. As generalized in FIG. 28, when the focus becomes a focus of an X-ray beam of an nch-th channel, a beam expressed by a broken-line arrow is selected as a path (a path of a channel angle $\gamma=\gamma m$ and a view angle $\beta=-\gamma m$) parallel with the reference path (a path of $\gamma=0$) from out of the fan beams.

As shown in FIG. 26, when a coordinate value on the s-axis of a central channel (Cpch) is a base value 0 in parallel beam data, a coordinate value S (ch) on the x-axis of a certain channel is obtained from the following Expression 3. In is assumed that a central channel in the fan beam data is represented by Cch, a central channel in the parallel beam data is represented by Cpch, and a sampling pitch of the parallel beam data is represented by dpch. FanAngle represents a fan angle, which is 2$\gamma m$. FOVr represents a radius of a maximum field of view.

A channel pch (ch) of parallel beam data in a certain channel is obtained from the following Expression 4.

A sampling pitch dpch of parallel beam data is obtained from the following Expression 5.

$$S(ch) = FOVr \times \sin(\gamma(ch)) \hspace{2cm} \text{(Expression 3)}$$
$$= FOVr \times \sin\left(\frac{FanAngle}{nch} \cdot (ch - Cch)\right)$$

$$pch(ch) = \frac{s(ch)}{dpch} + Cpch \hspace{2cm} \text{(Expression 4)}$$

where

Cch: central channel number in fan beam data

Cpch: central channel number in parallel beam data $$dpch = \frac{2 \times FOVr}{npch - 1} : \text{sampling pitch of parallel beam data} \hspace{1cm} \text{(Expression 5)}$$

Definitions of variables in the above expressions and the following expressions will be explained below.

Variables of fan beams are defined as follows. nch represents a number of channels of a detector, and Cch represents a central channel number. The central channel number Cch is different depending on QQ offset volume. QQ represents a QQ (Quarter-Quarter) offset element, which is determined based on a system in which the apparatus of the present embodiment is installed. The QQ offset is a method for improving installation space resolution by shifting a detector by a quarter of a channel in a channel direction from the center line. When the detector is offset correctly, the QQ is usually equal to 0.25. If the QQ offset is done correctly, the central channel number Cch becomes 448.25 when the number of channels is 896, for example.

nview represents a number of projections in one rotation, such as, for example, 900, 1,200, etc. raw(view, ch) represents raw data of a fan beam at a ch-th channel and at a view-th projection.

On the other hand, variables of parallel beams are defined as follows. npch represents a number of channels of parallel beam data, and Cpch represents a central channel number of parallel beam data. For example, when the number of channels is 896, the central channel number becomes 448.5. npview represents a number of projection data in one rotation in parallel beam data. praw (pview, pch) represents raw data of parallel beams at a pch-th channel and at a pview-th projection.

Further, pconv (pview, pch) represents convoluted data at a pch-th channel and at a pview-th projection filter-corrected by a convolution method. dc represents a pitch of resampling and centering points. ncp represents a number of resampling and centering points. pcent (pview, cp) represents resampled and centered data.

Further $\gamma$ represents a channel angle for an interested detector channel. $\gamma m$ represents a half of a fan angle. $\beta 0$ represents a view angle for interested projected data. $\beta$ represents a relative view angle for each channel originated from an interested projection.

Regarding functions, floor ( ) represents a function of converting to an integer by discarding. Pv (pch) represents a relative projection data number for pch-th channel.

Next, a channel number of parallel beam data is obtained.

First, the above Expression 3 is substituted by the Expression 4, to obtain the following Expression 6. This is then modified to obtain the following Expression 7.

$$pch(ch) = \frac{FOVr}{dpch} \times \sin\left(\frac{FanAngle}{nch} \cdot (ch - Cch)\right) + Cpch \quad \text{(Expression 6)}$$

$$\therefore ch(pch) = \quad \text{(Expression 7)}$$
$$\frac{nch}{FanAngle} \times \sin^{-1}\left(\frac{2 \cdot (pch - Cpch)}{npch - 1}\right) + Cch \equiv Pch(pch)$$

Then, the following Expression 8 is obtained, as shown in FIG. 26.

$$\beta(ch) = -\gamma(ch) = \frac{FanAngle}{nch} \cdot (Cch - ch) \quad \text{(Expression 8)}$$

$$\therefore Pv(pch) = \beta(ch(pch)) \cdot \frac{nview}{360} \quad \text{(Expression 9)}$$
$$\frac{FanAngle}{nch} \cdot \frac{nview}{360} \cdot$$
$$(Cch - Pch(pch))$$

$$v = view(pview) = \frac{2 \cdot npview}{nview} \cdot (pview - 1) + 1 \quad \text{(Expression 14)}$$

Accordingly, the relative projection data number Pv at the Pch-th channel can be obtained from the above Expression 9.

Based on the above process, parallel beams praw (pview, ch) in a necessary channel are selected. The parallel beams praw (pview, ch) in a necessary channel can be generated by the following expressions.

Figure 29:
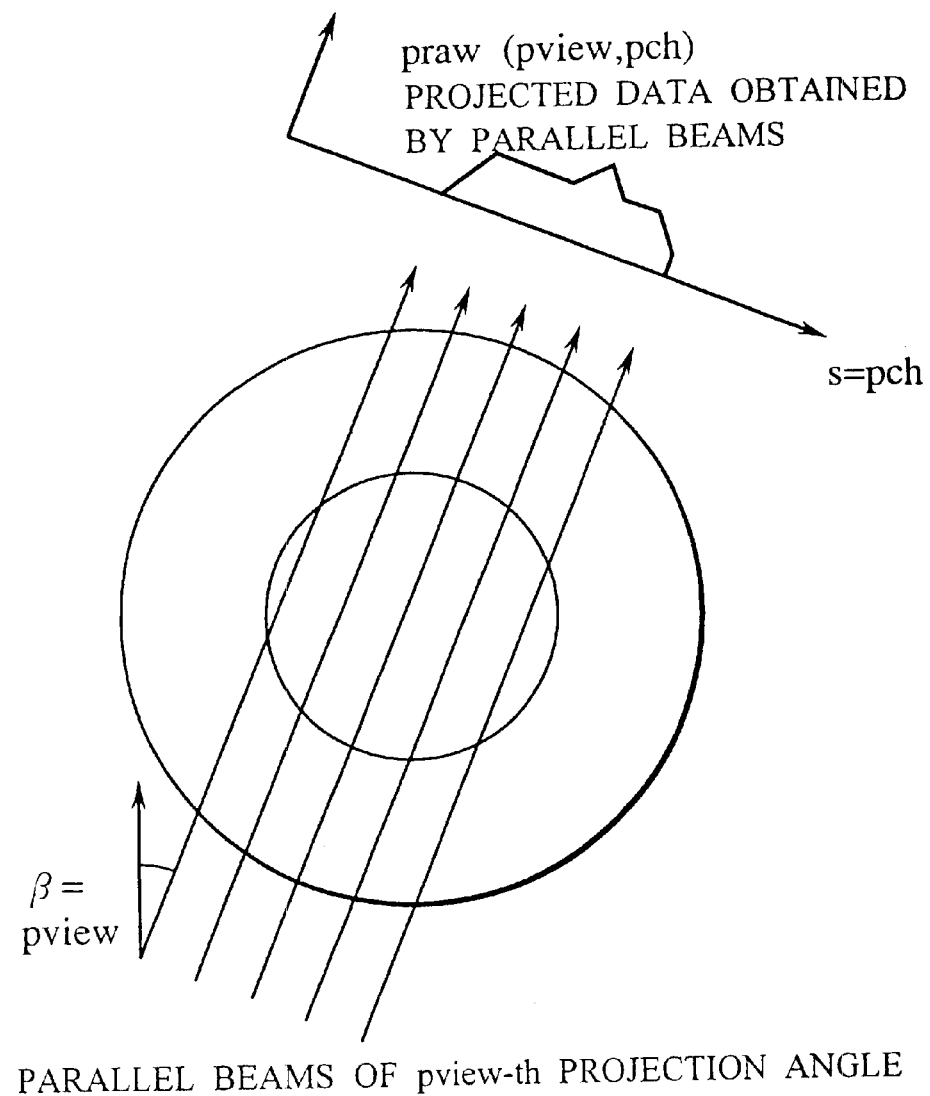
FIG. 29 is a view for explaining a relationship between generated parallel beams and a projection axis.

FIG. 29 shows a relationship between each channel of parallel beams selected for each view angle and the s-axis on which the parallel beams are projected. The s-axis is an axis perpendicular to a view angle at which a projection is to be carried out. A value of a positional correction in a channel direction to be described later is calculated based on this s-axis.

$$IPch = floor[Pch(pch)] \quad \text{(Expression 10)}$$

$$IPv = floor[Pv(pch)] \quad \text{(Expression 11)}$$

where floor ( ) represents a function for converting to an integer by discarding.

In this case, $$\beta 0(pview) = \frac{180 \cdot (pview - 1)}{npview} \quad \text{(Expression 12)}$$

$$\beta 0(view) = \frac{360 \cdot (view - 1)}{nview} \quad \text{(Expression 13)}$$

Next, weight functions are defined as shown in Expression 15 and Expression 16.

$$Wv = Pv[pch] - IPv \quad \text{(Expression 15)}$$

$$Wch = Pch[pch] - IPch \quad \text{(Expression 16)}$$

In other words, parallel beams praw (pview, ch) in a necessary channel are obtained by the following Expression 17.

$$praw(pview, pch) = raw(v + Pv(pch), pch) = [raw(v + IPv, IPch) + Wch \times (raw(v + IPv, IPch + 1) -$$
$$raw(v + IPv, IPch)) \times [1 - Wv] + [raw(v + IPv + 1, IPch + Wch \times (raw(v + IPv + 1, IPch + 1) - raw(v + IPv + 1, IPch))] \times Wv \quad \text{(Expression 17)}$$

In the present embodiment, the fan beam data-parallel beam data converter 120 converts the collected fan beams into parallel beams, according to the fan beam data-parallel beam data conversion method described above. The fan beam data-parallel beam data conversion described below is carried out in X-Y'-Z' coordinate system.

The fan beam data-parallel beam data conversion method applied to the fan beams can also be similarly applied to cone beams. The conversion method for converting from cone beams to parallel beams is disclosed, for example, in Japanese Laid-open Publication Hei 10-243941.

In this case, the shift correction value calculator 140 calculates the deviation amount Shift S(n) of an X-ray path in each detector row, based on the tilt data 160. When it is assumed that $\beta=0$ in the Y'-axis, the deviation amount Shift S(n) is obtained from the following Expression 18 when the deviation amount Shift Y(n) in the Y'-axial direction expressed by the Expression 1 is a deviation amount given to the s-axis.

$$\text{Shift } S(\text{slice}, \beta, n, \alpha) = \sin(\beta) \times \text{Shift Y' (slice}, n, \alpha) \quad \text{(Expression 18)}$$

Figure 30:
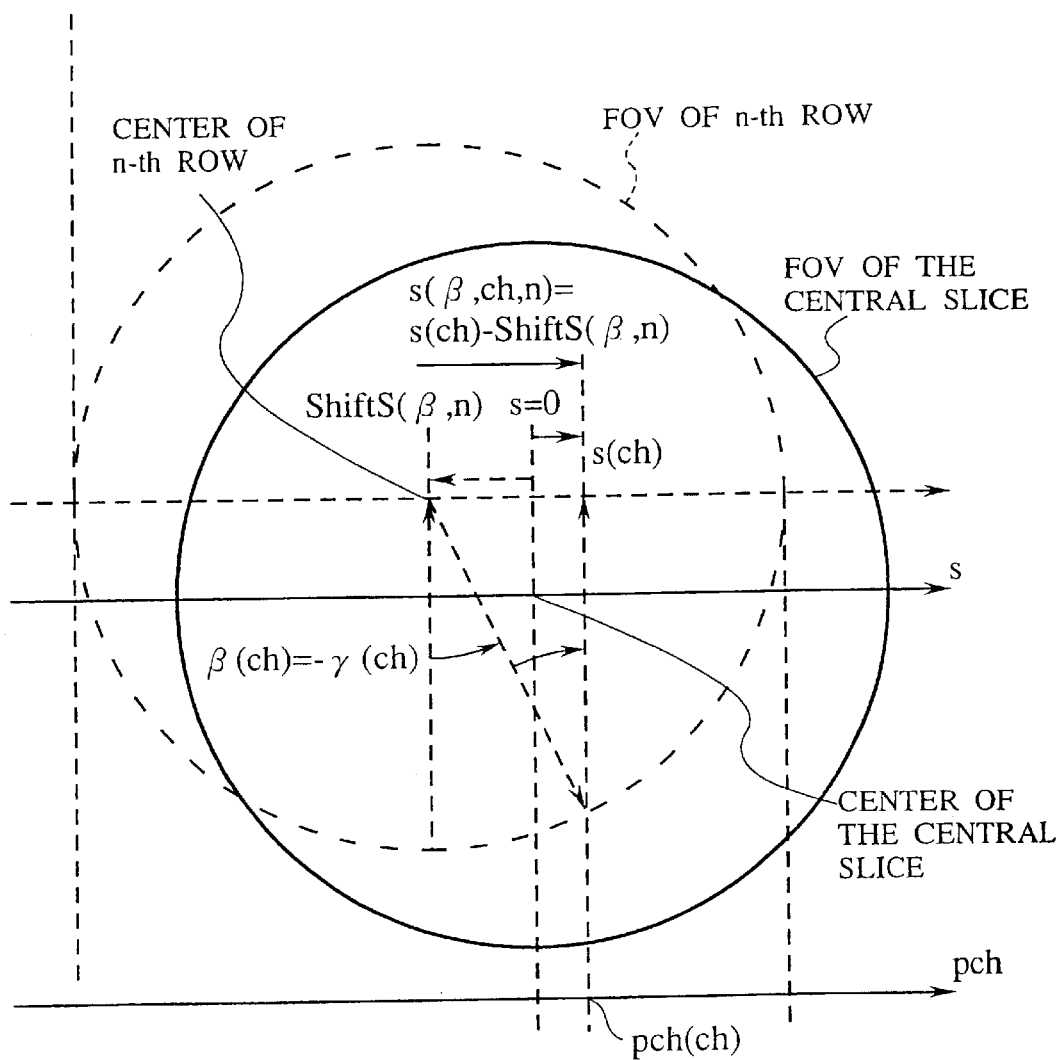
FIG. 30 is a view for explaining a fan beam data-parallel beam data conversion for each row of the detector and a shift amount between parallel beam data according to the embodiment of the present invention.

FIG. 30 shows a relationship between the FOV in the central slice and the FOV in the n-th row of the detector. Accordingly, as shown in FIG. 30, it can be understood that parallel beams in each row are generated by carrying out the above-described fan beam data-parallel beam data conversion by making a shift of Shift S.

In other words, the coordinates on the s-axis of a certain view angle in the n-th row can be obtained from the following Expression 3-2, by modifying the Expression 3, by taking into consideration the deviation amount Shift S on the s-axis obtained from the Expression 18.

The deviation amount Shift S becomes a function of a view angle β and a tilt angle α given as tilt data, a relative distance of the detector row from the central slice, and a slice thickness slice.

$$s(\beta, ch, n, \alpha) = FOVr \times \sin(\gamma(ch)) - ShiftS(\text{slice}, \beta, n, \alpha) \quad \text{(Expression 3-2)}$$
$$= FOVr \times \sin\left(\frac{FanAngle}{nch} \cdot (ch - Cch)\right) -$$
$$ShiftS(\text{slice}, \beta, n, \alpha)$$

$$pch(\beta, ch, n, \alpha) = \frac{s(\beta, ch, n, \alpha)}{dpch} + Cpch \quad \text{(Expression 4-2)}$$

where

Cch: a central channel number in fan beam data

Cpch: a central channel number in parallel beam data $dpch = 2 \times FOVr/npch - 1$:
a sampling pitch of
parallel beam data (Expression 5-2)=(Expression 5)

Next, when the Expression 3-2 is substituted by the Expression 4-2 in a manner similar to that of the fan beam data-parallel beam data conversion, the following Expression 6-2 can be obtained. When this is further modified, a result as shown in Expression 7-2 is obtained.

$$pch(b, ch, n, a) = \frac{FOVr}{dpch} \times \sin\frac{FanAngle}{nch} \cdot (ch - Cch) + Cpch - \frac{ShiftS(\text{slice}, b, n, a)}{dpch} \quad \text{(Expression 6-2)}$$

$$\therefore ch(\beta, pch, n, \alpha) = \frac{nch}{FanAngle} \times \sin^{-1}\left(\frac{2 \cdot \left(pch - Cpch + \frac{ShiftS(\text{slice}, \beta, n, \alpha)}{dpch}\right)}{npch - 1}\right) + Cch \quad \text{(Expression 7-2)}$$

$$\equiv Pch(\beta, pch, n, \alpha)$$

In this case, when a view angle is β, a detector row is n, a tilt angle is α, and a channel of parallel beams is pch from the following Expression 8-2 which is the same as the Expression 8, a relative projection data number Pv can be obtained from the following Expression 9-2.

$$\beta(ch) = -\gamma(ch) = \frac{FanAngle}{nch}(Cch - ch) \quad \text{(Expression 8-2) = (Expression 8)}$$

$$Pv(\beta, pch, n, \alpha) = \beta(ch(\beta, pch, n, \alpha)) \cdot \frac{nview}{360} \quad \text{(Expression 9-2)}$$
$$= \frac{FanAngle}{nch} \cdot \frac{nview}{360} \cdot$$
$$(Cch - Pch(\beta, pch, n, \alpha))$$

Accordingly, the parallel beams praw (pview, pch, n, α) in a necessary channel can be obtained from the following Expression 20.

$praw(pview, pch, n, \alpha) = raw(v + Pv(\beta, pch, n, \alpha),$
$Pch(\beta, pch, n, \alpha), n)$ (Expression 20)

The fan beam data-parallel beam data converter 120 obtains the parallel data praw by the fan beam data-parallel beam data conversion, and then makes the data correspond to the Z'-axis coordinate.

When the Z'-axis coordinate where the central slice exists in the first view is represented by Z0, and the helical pitch is represented by BedMoveZ, data collection coordinates Z' (pview, n) of each detector row on the Z' coordinates in the pview-th view are obtained from the following Expression 21. The helical pitch is defined as a move volume of a couch or a gantry in one rotation of the gantry on the Z-axis coordinate.

$$Z'(pview, n, \alpha) = ZNc'(pview, \alpha) + \quad \text{(Expression 21)}$$
$$\text{slice} \times (Nc - n)$$
$$= BedMoveZ \times \cos(\alpha) \times$$
$$\frac{pview - 1}{npview} + Z0 + \text{slice} \times$$
$$(Nc - n)$$

The fan beam data-parallel beam data converter 120 makes each parallel data correspond to the Z'-axis coordinate by using the above data collection coordinates Z' (pview, n). This converter 120 then outputs the corresponded parallel data to the interpolated-data generator 130.

(3) Helical Interpolation Processing

Next, the interpolated-data generator 130 performs a helical interpolation processing in a Z'-axial direction of the parallel beam data obtained by the fan beam data-parallel beam data conversion processing (2). It is noted that the helical interpolation can be employed from various interpolation methods in a helical scanning system. In this case, the Z'-axial direction is defined as a direction perpendicular to a tilt plane (a gantry rotation plane), and this is also defined as a slice direction.

For the helical interpolation herein, a generally-known helical interpolation method may be used. For example, there may be optionally used any one of a two-point interpolation method like the above-described adjacent interpolation method as disclosed in the Japanese Laid-open Publication Hei 9-234195, and a multi-point interpolation method like the filter interpolation method, the new opposite beam interpolation method, etc.

The interpolated-data generator 130 outputs to the image reconstructor 11 interpolated data of parallel beam data on the tilt surface obtained by interpolation in the Z'-axial direction.

(4) Image Reconstruction Processing

The image reconstructor 11 performs an image reconstruction based on the interpolated tilt-plane parallel data output from the interpolated-data generator 130 of the interpolation processor 10, by applying, for example, the filter correction back projection method described above to the parallel beams, in a similar manner to that applied to the helical scanning in the normal multi-slice CT apparatus. In this case, the back projection and image reconstruction method is not limited to the filter correction back projection method. It is also possible to carry out the image reconstruction based on any other arbitrary operational algorithm such as, for example, a generally-known sequential approximation method or a Fourier transformation method or the like, so long as the method employs a back projection corresponding to parallel beams.

Figure 31:
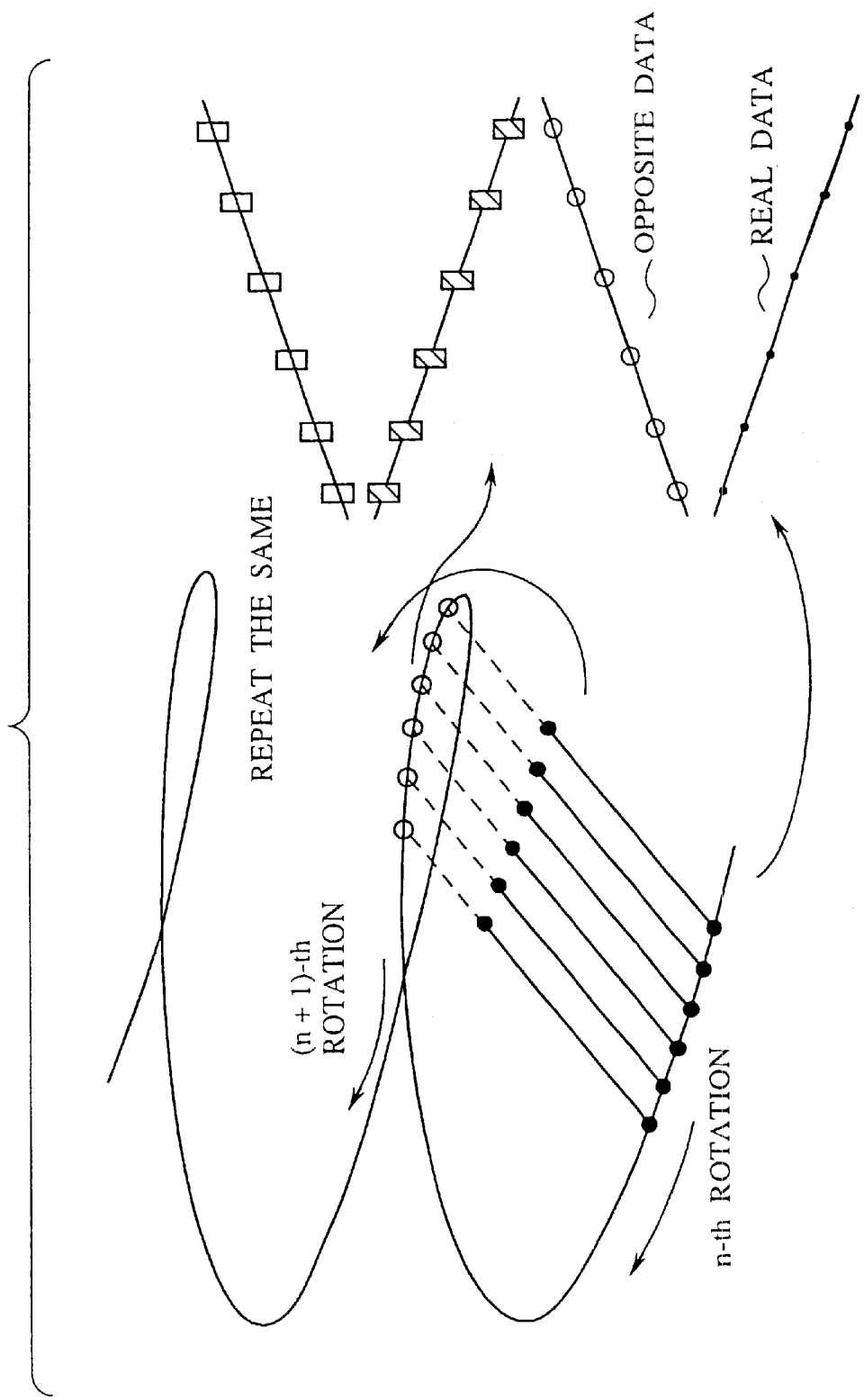
FIG. 31 is a view for explaining one example of a fan beam data-parallel beam data conversion in s single-slice CT.

The sampled data of parallel data used for the helical interpolation is laid out schematically such as shown in FIG. 31. For ease of explanation, FIG. 31 illustrates sampled data to be applied in the single-slice CT apparatus. However, in the case of the multi-slice CT apparatus used in the present embodiment, a plurality of loca are superimposed unlike a single locus as shown in FIG. 31.

According to the present embodiment, the following effects are obtained.

When the multi-slice CT apparatus has conducted a helical scanning by tilting the gantry, the apparatus first converts the data collected by detectors into parallel beam data. In the fan beam data-parallel beam data conversion, the apparatus calculates effective X-ray paths for each data on the image to be reconstructed by taking into consideration tilt data for tilting the gantry (such as a tilt angle, a view angle, a slice thickness, a relative distance from the central slice, etc.). Thus, the apparatus suitably selects data to be interpolated therebetween, and interpolates between the selected data in the Z'-axial direction (a slice direction), whereby reconstructing the image.

Therefore, it is also possible to obtain a high-precision reconstructed image at a high speed, even when the multi-slice CT apparatus carries out a helical scanning by tilting the gantry.

Next, there will be explained below a first modified example of the present embodiment.

In the above description, there has been explained an example of the case where a fan beam data-parallel beam data conversion is carried out in the X-Y'-Z' coordinate system. However, the fan beam data-parallel beam data conversion according to the present embodiment is not limited to the above.

A first modification of the present embodiment is a case where the fan beam data-parallel beam data conversion is conducted in the X-Y'-Z coordinate system using the Z-axis (body axis) as a base, and an interpolation processing is conducted in a Z-axial direction.

In the case of carrying out the fan beam data-parallel beam data conversion processing in the X-Y'-Z coordinate system, data in each row coincides with each other in a Z'-axial direction when X-ray paths in each row of the detector are observed from the Z'-axial direction. On the other hand, the respective data of the X-ray paths have a deviation as the gantry rotation progresses (that is, at the n-th rotation and (n+1)-th rotation). In other words, on the coordinates shown in FIG. 30, a circle in a solid line represents a FOV of the n-th rotation and a circle in a broken line represents a FOV in the (n+1)-th rotation of the same central slice. A deviation amount in an s-axial direction shown by Shift S is the same as that given by the Expression 18.

In this case, the Z-axis coordinate to which each parallel data corresponds is obtained from the following Expression 21-2 by modifying the Expression 21.

$$Z(pview, n, \alpha) = ZNc(pview, \alpha) + \frac{\text{slice} \times (Nc - n)}{\cos(\alpha)}$$

$$= BedMoveZ \times \frac{pview - 1}{npview} + Z0 + \text{slice} \times \frac{Nc - n}{\cos(\alpha)}$$

(Expression 21-2)

The interpolated-data generator 130 helically interpolates between the data after the fan beam data-parallel beam data conversion in a Z-axial (body axial) direction by using the Z-axis coordinate. All other structures and operations are the same as those described above, and their explanation will be omitted.

According to the first modified example, the effects similar to those of the above-described embodiment can be obtained.

Next, a second modification of the present embodiment will be explained.

In the above embodiment, the fan beam data-parallel beam data converter 120 has conducted the fan beam data-parallel beam data conversion by taking the deviation amount Shift S of the X-ray paths into consideration.

On the other hand, according to the second modification, the fan beam data-parallel beam data converter 120 generates helical orbit data of parallel beams for each data in each row, by disregarding the deviation amount Shift S at the time of the fan beam data-parallel beam data conversion.

Based on this parallel beam data, the interpolated-data generator 130 selects data to be interpolated therebetween by taking the deviation amount Shift S of the X-ray paths into consideration. More specifically, the interpolated-data generator 130 obtains the shift correction value Shift S calculated by the shift correction value calculator 140 by the control of the interpolation controller 150.

The interpolated-data generator 130 selects a pair of data (or data group) between which the interpolation is to be carried out, by shifting each parallel beam based on this shift correction value Shift S, thereby performing the helical interpolation processing. In carrying out this shift processing, it is necessary to conduct an interpolation depending on the case. All other structures and operations are similar to those of the above-described embodiment, and their explanation will be omitted.

Further, it is needless to mention that it is possible to carry out a fan beam data-parallel beam data conversion processing in the X-Y'-Z coordinate system by combining the second modification with the first modification, and to conduct a helical interpolation processing in a Z-axial direction.

According to the second modification, the effects similar to those of the above-described embodiment can be obtained.

Next, a third modification of the present embodiment will be explained.

In the above embodiment, the fan beam data-parallel beam data converter 120 has conducted the fan beam data-parallel beam data conversion by taking the deviation amount Shift S of the X-ray paths into consideration.

On the other hand, according to the third modification, an image reconstruction based on the back projection is carried out by taking the Shift S into consideration at the time of the back projection processing.

In the third modification, the fan beam data-parallel beam data converter 120 generates helical orbit data of parallel beams for each data in each row, by disregarding the deviation amount Shift S at the time of the fan beam data-parallel beam data conversion.

Further, the interpolated-data generator 130 conducts the helical interpolation processing based on this parallel data.

Figure 32:
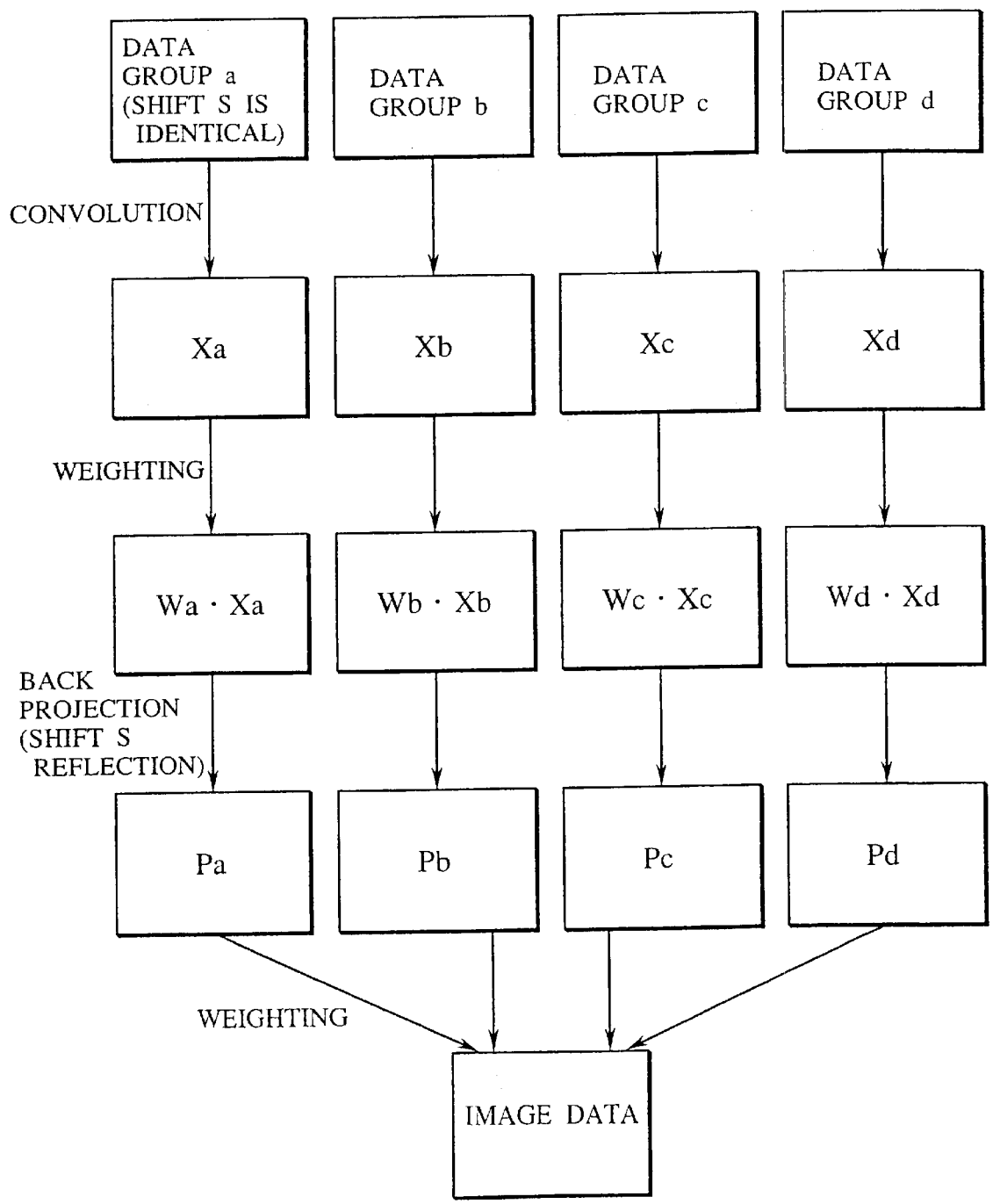
FIG. 32 is a view for explaining an image reconstruction process according to a third modification in the embodiment of the present invention.

FIG. 32 shows an image reconstruction processing carried out in the third modification.

The image reconstructor 11 performs a convolution processing for each of data of the identical view that is the data group having the identical shift correction value Shift S, with a reconstruction filter function. Next, the image reconstructor 11 weights the convoluted data. This weighting may be carried out by a weight function corresponding to the Z'-axis coordinate for each ray (channel) angle. Each data group is back projected along the effective path of X-rays by taking the deviation amount Shift S into consideration.

After the above-described processing has been carried out for the data necessary for the image reconstruction, the data are finally superimposed to obtain desired image data.

According to the third modification, the effects similar to those of the above embodiment can be obtained. Further, as the image reconstruction processing is conducted in parallel for the data at each view angle, and the reconstructed image data is finally obtained, it is also possible to conduct the image reconstruction processing at a high speed.

Next, a fourth modification of the present embodiment will be explained.

The X-ray CT apparatus according to the fourth modification includes unit for correcting a positional deviation of the converted parallel beam data in a slice direction, in addition to the processing of the above-described embodiment.

The fan beam data-parallel beam data converter 120 performs this conversion processing at a high speed by decreasing the calculation volume. Thus, positions of parallel beams in a slice direction are not taken into consideration in this processing. In the fourth modification, the positional deviation of the post-converted parallel beams in the slice direction is corrected. As this deviation amount can be obtained at the time of the fan beam data-parallel beam data conversion, the fan beam data-parallel beam data converter 120 may carry out the correction of this positional deviation and then output the parallel beam data of the corrected slicing position.

Further, the parallel beam data may be corrected to the right slicing position by reflecting this deviation amount to the weighted data that changes depending on the channel, at the time of the back projection processing conducted by the image reconstructor 11.

Other processes are the same as those of the above-described embodiment, and hence their explanation will be omitted.

According to the fourth modification, there is an effect that it is possible to obtain image data of high-precision picture quality by decreasing blurs in the image data for image reconstruction, in addition to the effects obtained in the above-described embodiment.

It is possible to implement the above-described modifications individually or by suitably combining them.

The above-described embodiment including the modifications shows only one aspect of the present invention, and the present invention is not limited to this embodiment.

For example, in the above-described helical interpolation processing, the interpolation may be carried out by using opposite data or by using only real data. Further, this invention can also be applied similarly to a fourth generation scanning system CT apparatus that obtains projection data by rotating around the subject an X-ray tube disposed between the subject and detectors, with these detectors fixedly disposed in parallel around the whole periphery of the rotation center.

Further, for carrying out the helical scanning, it may be so arranged that two gantries move for one fixed couch. The gantry 2 may not be tilted but the couch 1 may be tilted and moved in a direction not a horizontal direction. Further, the original data may be defined according to so-called a virtual focusing system that makes variable the FCD by taking into consideration that the data collection time is slightly different for each detector element. While the image reconstruction based on the fan beam back projection system has been explained in the above-described embodiment, it is also possible to apply the present invention to an image reconstruction system based on cone beams by using a similar processing. When the image reconstruction is conducted based on cone beams, data and weight for back projecting for each voxel are selected, by taking the spread of the cone-direction beams into consideration. In this case, the deviation of the X-ray paths is corrected corresponding to each row of the detector.

In other words, it is needless to mention that the present invention can be applied through various modifications according to designs and the like so long as the modifications are within the scope not deviating from the technical idea relating to the present invention that, in conducting a tilt helical scanning, the multi-slice CT apparatus generates parallel beams (or suitably selects data) by calculating the effective path of X-ray beams for each data on a reconstructed image by taking the tilt angle into consideration, and helically interpolates between the parallel beams thereby reconstructing an image.

In summary, the X-ray CT apparatus according to the present invention provides following effects.

The present invention provides a function of performing a helical interpolation and image reconstruction through the conduction of a helical scanning by tilting the gantry in the multi-slice CT apparatus.

This function is exhibited with a particular effect in the multi-slice CT apparatus that has a larger width in the slice direction of each detector row than the width in a channel direction.

As explained above, according to the present invention, it is possible to achieve a tilt scanning in the helical scanning of the multi-slice CT apparatus which it has not been possible to effectively carry out by the conventional techniques. Further, it is possible to achieve collection of various data desired in the clinical field of helical scanning by using the multi-slice CT apparatus for a high-speed and high-precision operation.

It is to be noted that, besides those already mentioned above, many modifications and variations of the above embodiments may be made without departing from the novel and advantageous features of the present invention. Accordingly, all such modifications and variation are intended to be included within the scope of the invention.

What is claimed is:

1. An X-ray computed tomography apparatus, comprising:

a helical data collector configured to collect helical data while at least one of a gantry and a couch is moved by a moving device along a body axial direction of an object on the couch in a state that at least one of the gantry and the couch is tilted, including,
   an X-ray source configured to generate X-rays, and
   a detector configured to have detector elements laid out in a plurality of rows along the body axial direction; and
a data processor configured to reconstruct an image based on the helical data collected by said helical data collector, including,
   a shift data generator configured to generate shift data for correcting a deviation of X-ray paths due to a tilt of the couch or the gantry, said shift data being obtained based on an angle of the tilt.

2. The X-ray computed tomography apparatus according to claim 1, wherein
the data processor interpolates between the helical data based on a tilt angle of either the couch or the gantry.

3. The X-ray computed tomography apparatus according to claim 1, wherein
the data processor interpolates between the helical data in a body axial direction or a slice direction.

4. The X-ray computed tomography apparatus according to claim 1, wherein
said data processor further includes:
a data converter configured to convert the helical data into parallel beam data; and
a corrector configured to correct the parallel beam data based on the shift data.

5. The X-ray computed tomography apparatus according to claim 4, wherein
the data converter converts the helical data into the parallel beam data based on the shift data.

6. The X-ray computed tomography apparatus according to claim 4, wherein
the data processor performs helical interpolation between the parallel beam data based on the shift data.

7. The X-ray computed tomography apparatus according to claim 4, wherein
the data converter converts the helical data into the parallel beam data by selecting X-ray path data one by one that is parallel with a reference path, for each fan beam data at each view angle.

8. The X-ray computed tomography apparatus according to claim 1 wherein
the angle is a tilt angle of the gantry set as a tilt angle $\alpha$.

9. The X-ray computed tomography apparatus according to claim 1, wherein
the shift data is obtained based on at least one of the tilt angle, a slice thickness, a view angle, and a number of rows of the detectors.

10. The X-ray computed tomography apparatus according to claim 9, wherein
the shift data is further obtained based on a relative distance between a central slice and each of the detector rows.

11. The X-ray computed tomography apparatus according to claim 10, wherein
the relative distance is obtained based on the number of the detectors and row numbers.

12. The X-ray computed tomography apparatus according to claim 4, wherein
the data processor reconstructs an image by helical interpolation between parallel beam data converted by the data converter.

13. The X-ray computed tomography apparatus according to claim 12, wherein
the data processor generates interpolated data by adding weighted multi-point sampled data.

14. The X-ray computed tomography apparatus according to claim 4, wherein
the data processor reconstructs image data by helical interpolation between parallel beam data output by the data converter, and by back projecting the helically interpolated data based on the shift data.

15. The X-ray computed tomography apparatus according to claim 14, wherein
the data processor reconstructs image data by carrying out convolution and back projection to each of data of identical view angle, and by superimposing each projected data.

16. The X-ray computed tomography apparatus according to claim 4, wherein
the data processor further includes:
a data corrector for correcting a deviation of slicing positions of the parallel beam data.

* * * * *